United States Patent
Kinoshita et al.

(10) Patent No.: US 10,137,310 B2
(45) Date of Patent: Nov. 27, 2018

(54) BODY HAIR LUMINESCENCE AESTHETIC DEVICE

(71) Applicant: Panasonic Intellectual Property Management Co., Ltd., Osaka (JP)

(72) Inventors: Masato Kinoshita, Shiga (JP); Kaori Suzuki, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 114 days.

(21) Appl. No.: 14/418,346

(22) PCT Filed: Jan. 10, 2014

(86) PCT No.: PCT/JP2014/000094
§ 371 (c)(1),
(2) Date: Jan. 29, 2015

(87) PCT Pub. No.: WO2014/129101
PCT Pub. Date: Aug. 28, 2014

(65) Prior Publication Data
US 2015/0224338 A1   Aug. 13, 2015

(30) Foreign Application Priority Data
Feb. 22, 2013  (JP) ................................. 2013-033889

(51) Int. Cl.
*A61N 5/00*  (2006.01)
*A61N 5/06*  (2006.01)
(Continued)

(52) U.S. Cl.
CPC .. *A61N 5/0617* (2013.01); *A61B 2018/00476* (2013.01); *A61B 2018/1807* (2013.01);
(Continued)

(58) Field of Classification Search
CPC .......... A61N 5/0617; A61N 2005/0644; A61N 2005/0662; A61B 2018/1807
See application file for complete search history.

(56) References Cited

U.S. PATENT DOCUMENTS

| | | | |
|---|---|---|---|
| 4,792,341 A | * | 12/1988 | Kozikowski ........... A45D 19/00 204/157.61 |
| 5,626,631 A | | 5/1997 | Eckhouse |

(Continued)

FOREIGN PATENT DOCUMENTS

| | | |
|---|---|---|
| GB | 1316803 A | 5/1973 |
| JP | 2006-149489 A | 6/2006 |

(Continued)

OTHER PUBLICATIONS

Extended European Search Report issued in European Application No. 14754211.2 dated Feb. 18, 2016.
(Continued)

*Primary Examiner* — Amanda Hulbert
*Assistant Examiner* — Amanda Steinberg
(74) *Attorney, Agent, or Firm* — McDermott Will & Emery LLP

(57) ABSTRACT

An optical cosmetic device for body hair includes an optical system that emits cosmetic light for body hair. The optical system includes a light source, a control unit that controls at least one of a voltage and a current supplied to the light source, and an optical filter that changes a spectrum of light emitted from the light source. An intensity integral of the cosmetic light for body hair in a wavelength range of 400 to 700 nm is larger than that in a wavelength range of 700 to 1200 nm. An intensity integral of the cosmetic light for body hair in a wavelength range of 400 to 500 nm is smaller than that in a wavelength range of 500 to 600 nm. The largest one
(Continued)

of intensity peaks of the cosmetic light for body hair is in a wavelength range of 400 to 570 nm.

16 Claims, 8 Drawing Sheets

(51) Int. Cl.
  *A61B 18/00* (2006.01)
  *A61B 18/18* (2006.01)
(52) U.S. Cl.
  CPC ............... *A61N 2005/0644* (2013.01); *A61N 2005/0662* (2013.01)

(56) References Cited

U.S. PATENT DOCUMENTS

| | | | | |
|---|---|---|---|---|
| 5,885,273 | A * | 3/1999 | Eckhouse | A61B 18/203 606/10 |
| 6,280,438 | B1 * | 8/2001 | Eckhouse | A61B 18/203 606/9 |
| 7,762,964 | B2 * | 7/2010 | Slatkine | A61B 18/203 601/15 |
| 8,226,696 | B1 | 7/2012 | Christiansen et al. | |
| 2004/0010298 | A1 | 1/2004 | Altshuler et al. | |
| 2004/0147985 | A1 * | 7/2004 | MacFarland | A61B 18/203 607/90 |
| 2005/0107853 | A1 * | 5/2005 | Krespi | A61B 18/18 607/89 |
| 2007/0027440 | A1 * | 2/2007 | Altshuler | A61B 18/203 606/9 |
| 2007/0239144 | A1 | 10/2007 | Korenberg | |
| 2008/0225524 | A1 * | 9/2008 | Lee | A61B 18/203 362/293 |
| 2008/0266690 | A1 | 10/2008 | Toda et al. | |
| 2010/0131035 | A1 | 5/2010 | Hamada et al. | |
| 2012/0172949 | A1 | 7/2012 | Wagenaar Cacciola et al. | |
| 2013/0030421 | A1 * | 1/2013 | Gomez De Diego | A61B 18/203 606/3 |

FOREIGN PATENT DOCUMENTS

| | | |
|---|---|---|
| JP | 2008-029811 A | 2/2008 |
| JP | 2008-188258 A | 8/2008 |
| JP | 2009-538157 A | 11/2009 |
| JP | 2011-167450 A | 9/2011 |
| JP | 2012-531239 A | 12/2012 |
| WO | 2010/079463 A1 | 7/2010 |
| WO | 2011/070795 A1 | 6/2011 |

OTHER PUBLICATIONS

English Translation of International Preliminary Report on Patentability issued in International Application No. PCT/JP20014/000094 dated Aug. 25, 2015.
International Search Report issued in PCT/JP2014/000094, dated Apr. 8, 2014, with English translation.
Japanese Office Action issued in Japanese Application No. 2013-033889, dated Jul. 5, 2016, with English Translation.

* cited by examiner

BODY HAIR LUMINESCENCE AESTHETIC DEVICE

RELATED APPLICATIONS

This application is the U.S. National Phase under 35 U.S.C. § 371 of International Application No. PCT/JP2014/000094, filed on Jan. 10, 2014, which in turn claims the benefit of Japanese Application No. 2013-033889, filed on Feb. 22, 2013, the disclosures of which Applications are incorporated by reference herein.

TECHNICAL FIELD

The present invention relates to an optical cosmetic device for body hair.

BACKGROUND ART

Patent document 1 describes a known optical cosmetic device for body hair. The optical cosmetic device for body hair described in patent document 1 irradiates areas around hair roots with light having a wavelength of 400 to 600 nm and an energy density of 0.01 to 1 (J/cm$^2$).

Patent Document 1: Japanese Laid-Open Patent Publication No. 2008-29811

SUMMARY OF THE INVENTION

The inventors of the present application have studied the absorbance of oxyhemoglobin and melanin and identified the spectrum of light that is less likely to cause unwanted side effects, such as skin inflammation, and is capable of inhibiting the growth of body hair. Although patent document 1 describes the absorbance of melanin in paragraph [0016], the document does not refer to the absorbance of melanin in association with side effects on the skin or with inhibited growth of body hair.

It is an object of the invention to provide an optical cosmetic device for body hair that is less likely to cause unwanted side effects on the skin and is capable of inhibiting the growth of body hair.

An optical cosmetic device for body hair according to one embodiment of the present invention includes an optical system that emits cosmetic light for body hair. An intensity integral of the cosmetic light for body hair is larger in a wavelength range of 400 to 700 nm than in a wavelength range of 700 to 1200 nm, and an intensity integral of the cosmetic light for body hair is smaller in a wavelength range of 400 to 500 nm than in a wavelength range of 500 to 600 nm.

In one example, the cosmetic light for body hair includes a plurality of intensity peaks in the wavelength range of 400 to 700 nm, and the largest one of the plurality of intensity peaks is included in the wavelength range of 500 to 600 nm.

In one example, the cosmetic light for body hair includes a plurality of intensity peaks in the wavelength range of 400 to 700 nm, and the smallest one of the plurality of intensity peaks is included in the wavelength range of 400 to 500 nm.

In one example, the cosmetic light for body hair does has no intensity peaks in a wavelength range of 400 to 440 nm that includes a first absorbance peak of oxyhemoglobin.

In one example, the cosmetic light for body hair has no intensity peaks in a wavelength range of 530 to 570 nm that includes a second absorbance peak of oxyhemoglobin.

In one example, the cosmetic light for body hair has an energy density of 0.2 to 1.5 J/cm$^2$.

The inventors of the present application have studied the absorbance spectrum of oxyhemoglobin as well as the absorbance rate of melanin, and identified the spectrum of cosmetic light for body hair based on the findings of the study. The inventors have summarized the experimental results for oxyhemoglobin and melanin, and defined the relationship between the spectrum of cosmetic light for body hair and the reduction of side effects as well as the improvement in the cosmetic treatment effect. The side effects reduction herein refers to reducing the likelihood of unwanted side effects on the skin. The improvement in the cosmetic treatment effect herein refers to improving the body hair cosmetic treatment effect to inhibit the growth of body hair. The body hair cosmetic treatment effect herein refers to the effectiveness of inhibiting hair growth in a living body or removing hair from a living body. Inhibiting hair growth herein refers to an effect in which the reproduction or the growth of body hair is inhibited in a living body. Removing hair refers to an effect in which body hair is removed from a living body.

The unwanted side effects on the skin have a correlation with the amount of light energy absorbed by oxyhemoglobin. The unwanted side effects on the skin may increase as the amount of light energy absorbed by oxyhemoglobin increases. Light in a wavelength range of 400 to 500 nm is more easily absorbed by oxyhemoglobin than light in a wavelength range of 500 to 600 nm and light in a wavelength range of 600 to 700 nm. To mainly reduce unwanted side effects on the skin, it is preferable that light with a shorter wavelength within the wavelength range of 400 to 700 nm has a smaller amount of light energy.

The body hair cosmetic treatment effect has a correlation with the amount of light energy absorbed by oxyhemoglobin. The body hair cosmetic treatment effect may be improved when there is an increase in the amount of light energy absorbed by melanin in body hair. In the wavelength range of 400 to 700 nm, the melanin of body hair absorbs light more easily as the wavelength of the emitted light becomes shorter. Thus, to mainly improve the body hair cosmetic treatment effect, it is preferable that the amount of light energy be increased at short wavelengths in the wavelength range of 400 to 700 nm.

The facts described above indicate the following. The light irradiating the body hair is less likely to cause unwanted side effects on the skin when its light energy is small in the wavelength range of 400 to 500 nm. However, melanin absorbing a smaller amount of light energy may lead to an insufficient body hair cosmetic treatment effect. The light irradiating the body hair is likely to improve the body hair cosmetic treatment effect when its light energy in the wavelength length of 400 to 500 nm is large. However, oxyhemoglobin absorbing a larger amount of light energy may increase the likelihood of unwanted side effects on the skin.

Based on these findings, the inventors of the present application have identified cosmetic light for body hair that achieves a proper balance between the amount of light energy absorbed by oxyhemoglobin and the amount of light energy absorbed by melanin. Such cosmetic light for body hair can reduce the side effects and improve the cosmetic treatment effect. The inventors of the present application have defined such cosmetic light for body hair with the relationship between the amount of light energy in the wavelength range of 400 to 500 nm and the amount of light energy in the wavelength range of 500 to 600 nm. The cosmetic light for body hair has a smaller amount of light energy in the wavelength range of 400 to 500 nm than in the wavelength range of 500 to 600 nm. The amount of light energy is defined by the intensity integral in the wavelength range of 400 to 500 nm and the intensity integral in the wavelength range of 500 to 600 nm.

The cosmetic light for body hair has a smaller amount of light energy in the wavelength range of 400 to 500 nm than in the wavelength range of 500 to 600 nm. Such cosmetic light is less easily absorbed by oxyhemoglobin and is less likely to cause unwanted side effects on the skin. The cosmetic light for body hair has a larger intensity integral in the wavelength range of 400 to 700 nm than in the wavelength range of 700 to 1200 nm, and thus is more likely to improve the body hair cosmetic treatment effect.

EFFECTS OF THE INVENTION

The optical cosmetic device for body hair of the present invention is less likely to cause unwanted side effects on the skin and is capable of inhibiting the growth of body hair.

DESCRIPTION OF EMBODIMENTS

First Embodiment

Figure 1:
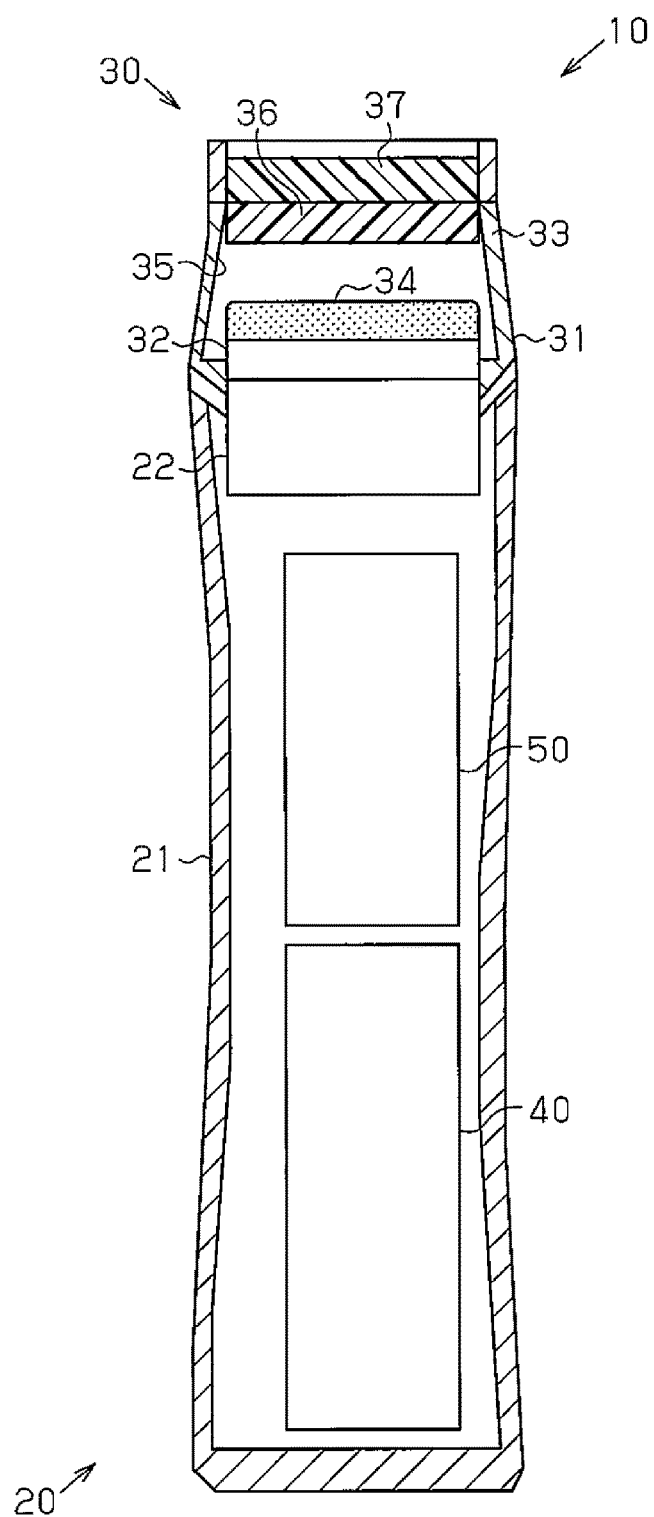
FIG. 1 is a schematic diagram of an optical cosmetic device for body hair according to a first embodiment.

One embodiment of an optical cosmetic device 10 for body hair has the structure shown in FIG. 1. The optical cosmetic device 10 for body hair includes an optical system that irradiates a living body with cosmetic light for body hair to improve the cosmetic treatment effect on the living body. The optical cosmetic device 10 for body hair includes a main body 20, a light source unit 30, a power supply circuit unit 40, and a control unit 50.

The main body 20 is shaped to so that it can be held by a user. The main body 20 includes, for example, a body housing 21 and a body connector 22. The main body 20 includes multiple components that are integrated together.

The body housing 21 is formed from, for example, a resin material. The body housing 21 is vertically long. The body housing 21 has an internal space. The body housing 21 accommodates the power supply circuit unit 40 and the control unit 50 in its internal space.

The body connector 22 is connected to the body housing 21. The body connector 22 is electrically connected to the power supply circuit unit 40. The body connector 22 is mechanically connectable to and separable from a light source connector 32. When mechanically connected to the light source connector 32, the body connector 22 is electrically connected to the light source connector 32.

The light source unit 30 may be, for example, an attachment that can be attached to or detached from the main body 20. The light source unit 30 includes, for example, a light source housing 31, the light source connector 32, a filter mounting part 33, a light source 34, a reflector 35, a lens 36, and an optical filter 37. The light source unit 30 includes multiple components integrated together. The light source unit 30 includes the optical filter 37 that is replaceable with another optical filter. The light source unit 30 can change the spectrum of light to be applied from the light source 34 in accordance with the type of optical filter 37.

The light source housing 31 may be formed from a resin material. The light source housing 31 has a shape similar to a cylinder. The light source housing 31 has an internal space. The light source housing 31 accommodates the light source 34, the reflector 35, and the lens 36 in its internal space. The light source housing 31 can prevent foreign matter entry, and prevent external dust or other foreign matter from entering the internal space of the light source housing 31. The light source housing 31 absorbs light with a specific wavelength range. In one example, the light source housing 31 absorbs light with a wavelength longer than 700 nm. In another example, the light source housing 31 absorbs light with a wavelength longer than 700 nm and not longer than 1200 nm.

The light source connector 32 is connected to the light source housing 31. The light source connector 32 is electrically connected to the light source 34. The light source connector 32 is mechanically connectable to and separable from the body connector 22. When mechanically connected to the body connector 22, the light source connector 32 is electrically connected to the body connector 22.

The filter mounting part 33 has a shape similar to an annular ring. The filter mounting part 33 is arranged at an opening of the light source housing 31. The filter mounting part 33 is connected to the light source housing 31. The filter mounting part 33 is mechanically connectable to and separable from the optical filter 37.

The light source 34 is arranged in the internal space of the light source housing 31. The light source 34 is connected to the light source housing 31. The light source 34 is electrically connected to the light source connector 32. The light source 34 includes, for example, a xenon flash lamp, a laser, a light-emitting diode (LED), or an organic electroluminescence (EL). In one example, the light source 34, which is a xenon flash lamp, applies light containing components having wavelengths of 400 to 1200 nm.

The reflector 35 is formed from a highly reflective material. The reflector 35 is formed from, for example, a metal material, a resin material, or ceramic. The reflector 35 preferably has a surface processed to increase the reflectivity of light applied from the light source 34. The processed surface includes, for example, a mirrored surface, a metal-coated surface, or a surface with a film of deposited metal.

The reflector 35 is connected to an inner circumferential surface of the light source housing 31. The reflector 35 reflects light from the light source 34 toward the opening of the light source housing 31. The reflector 35 may include a dielectric film that reflects light with a specific wavelength range. The dielectric film may reflect, for example, light with wavelengths that can contribute to improving the cosmetic treatment effect of body hair. In one example, the reflector 35 absorbs light with a wavelength longer than 700 nm. In another example, the reflector 35 absorbs light with a wavelength longer than 700 nm and not longer than 1200 nm.

The lens 36 has a shape similar to a circle. The lens 36 is formed from a material having high light transmittance in a specific wavelength range. The lens 36 is, for example, formed from a material with high transmittance in a wavelength range of visible light and in a wavelength range of infrared light. The lens 36 is, for example, formed from acrylic, polycarbonate, or glass. The lens 36 is arranged in the internal space of the light source housing 31. The lens 36 is connected to the light source housing 31. The lens 36 diffuses light reflected from the reflector 35 toward the outside of the light source housing 31. The lens 36 can smooth the energy density of light measured at an external position separated from the opening of the light source housing 31 by a predetermined distance (energy density smoothing structure).

The optical filter 37 is formed mainly from glass. The optical filter 37 has a shape similar to a circle. The optical filter 37 is arranged at the opening of the light source housing 31. The optical filter 37 is arranged outward from the light source housing 31 with respect to the lens 36. The optical filter 37 is placed on the lens 36 to cover an outer surface of the lens 36. The optical filter 37 is mechanically connectable to and separable from the filter mounting part 33. The optical filter 37 is mechanically connected to the filter mounting part 33. The optical filter 37 may be a wavelength selective filter that can absorb light with a specific wavelength range. In one example, the optical filter 37 may absorb light with a wavelength outside a range of 400 to 700 nm.

The light absorbing structure of the optical filter 37 may include, for example, a glass base containing a light absorbing material. The optical filter 37 includes a light absorbing film that may be, for example, a metal film, a dielectric film, or a composite film containing metal and dielectric. The metal film may be, for example, a film of titanium oxide, zirconium oxide, or aluminum oxide. Another example of the light absorbing structure includes a glass base having a light absorbing film on its surface. The light absorbing material includes, for example, metal particles or an oxide of metal particles. The metal may be, for example, gold, silver, copper, lead, zinc, cobalt, or manganese. The light absorbing film may have a monolayer or multilayer structure. The multilayer structure of the light absorbing film is formed by, for example, vacuum vapor deposition. The light absorbing structure absorbs, for example, light with a wavelength longer than 700 nm. The light absorbing structure absorbs, for example, light with a wavelength longer than 700 nm and not longer than 1200 nm.

The light source housing 31, the reflector 35, and the optical filter 37 absorb light with a wavelength longer than 700 nm and not longer than 1200 nm. This structure reduces the temperature increase of the optical filter 37, as compared with the structure in which at least one of the light source housing 31 or the reflector 35 is assumed to absorb no light.

The cosmetic light for body hair that has passed through the optical filter 37 preferably contains components only within the wavelength range of 400 to 700 nm. The cosmetic light for body hair that has passed through the optical filter 37 may also contain components outside the wavelength range of 400 to 700 nm. In this case, the components outside the wavelength range of 400 to 700 nm have a sufficiently smaller amount of light energy than the components within the wavelength range of 400 to 700 nm. Thus, the components outside the wavelength range of 400 to 700 nm have a small influence on the body hair or the skin.

The power supply circuit unit 40 is accommodated in the internal space of the body housing 21. The power supply circuit unit 40 supplies power from a power supply incorporated in the body housing 21 or from an external power supply to the light source 34.

The control unit 50 is accommodated in the internal space of the body housing 21. The control unit 50 controls at least one of a voltage or a current supplied to the light source 34 to control light applied from the light source 34. For example, the control unit 50 adjusts the total amount of light energy of light applied from the light source 34 per irradiation, and the time for which light is applied from the light source 34 per irradiation (hereafter, irradiation time), and/or the energy density of light applied from the light source 34 per irradiation. In one example, the irradiation time per irradiation is set in a range of 600 μs to 2 ms. The energy density of light per irradiation is set in a range of 0.2 to 1.5 (J/cm$^2$).

Figure 4:
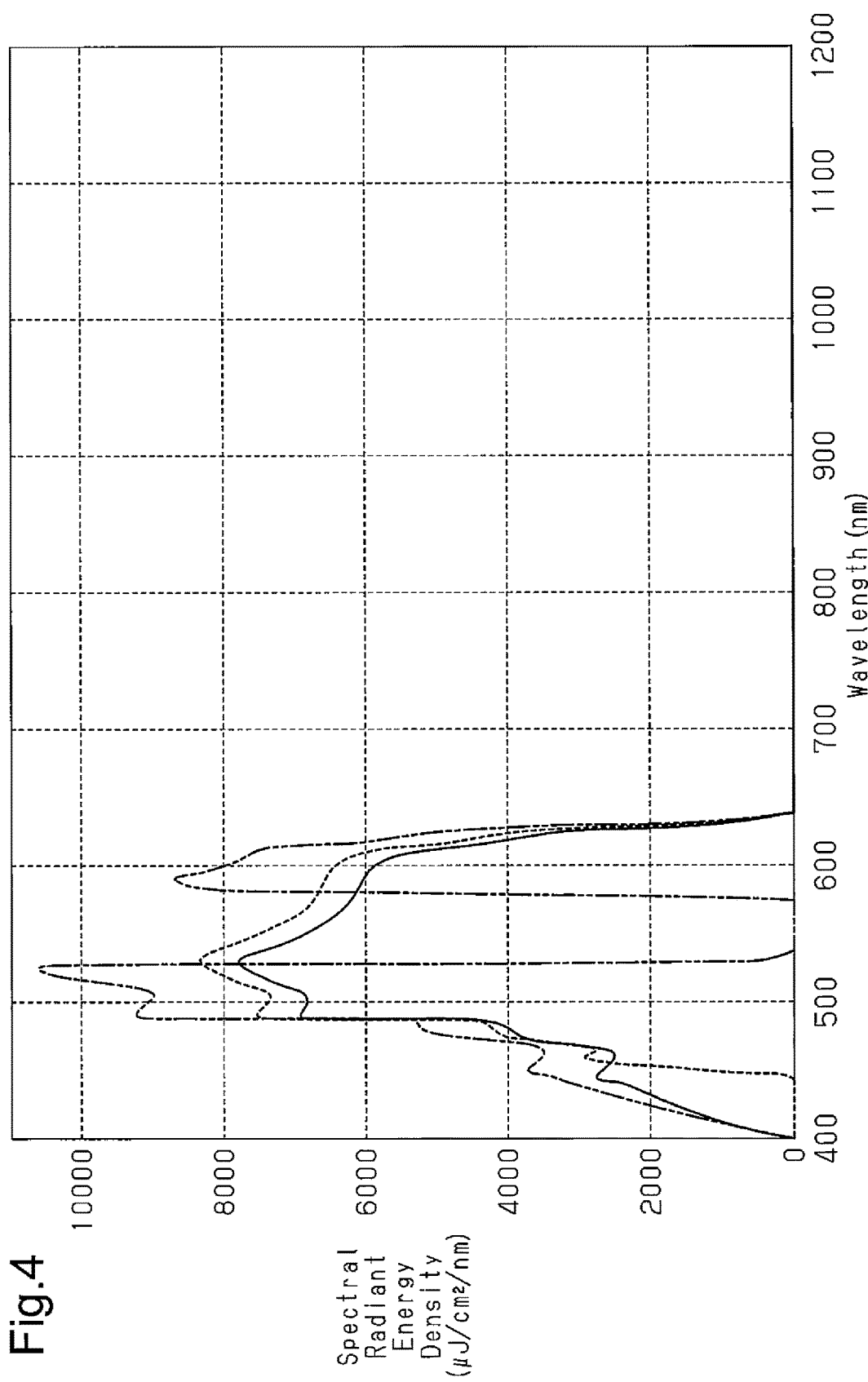
FIG. 4 is a graph showing the spectra of cosmetic light for body hair emitted from optical cosmetic devices for body hair in first to third embodiments.
Figure 5:
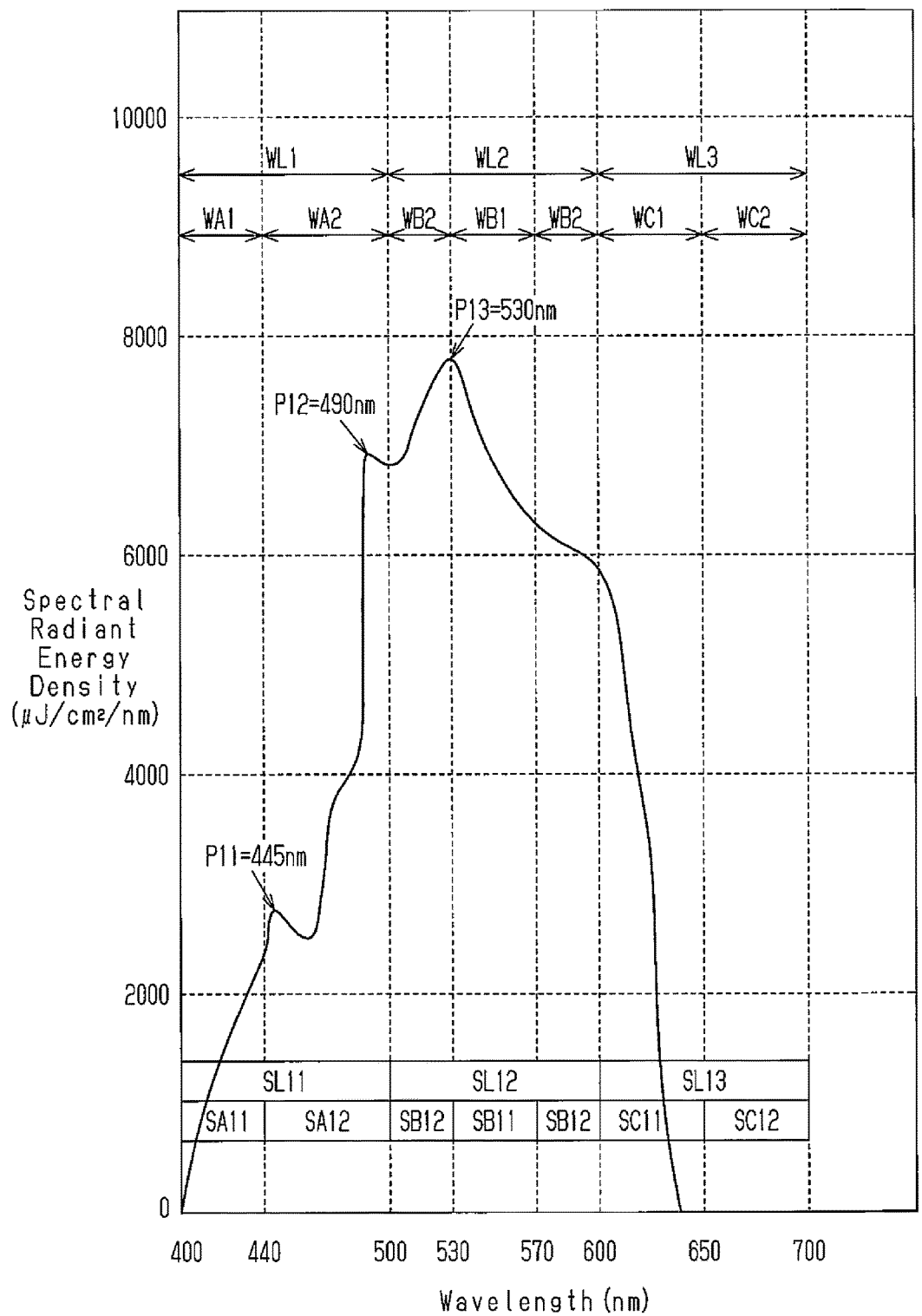
FIG. 5 is a graph partially showing the spectrum of cosmetic light for body hair emitted from the optical cosmetic device for body hair in the first embodiment.
Figure 6:
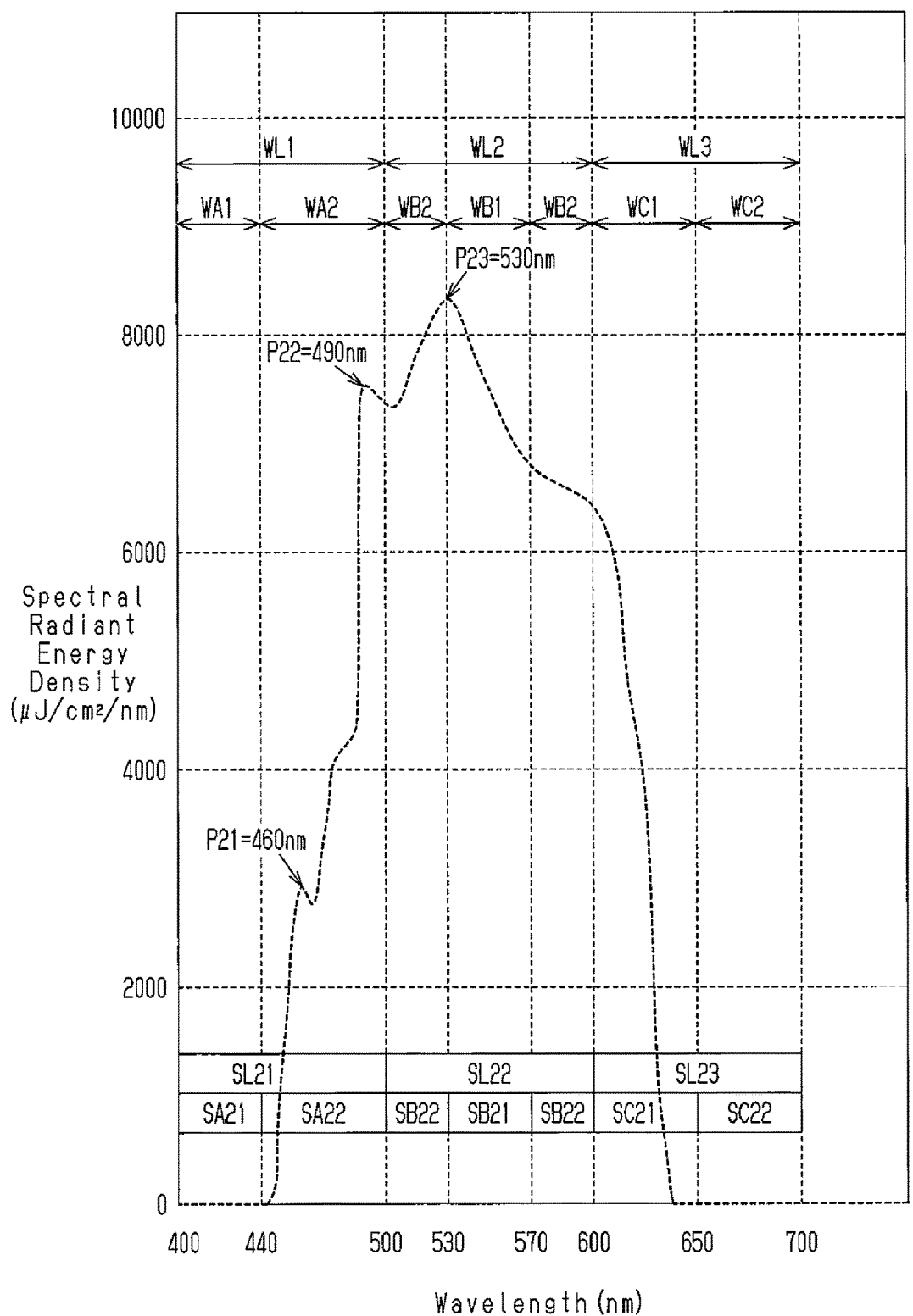
FIG. 6 is a graph partially showing the spectrum of cosmetic light for body hair applied from the optical cosmetic device for body hair in the second embodiment.
Figure 7:
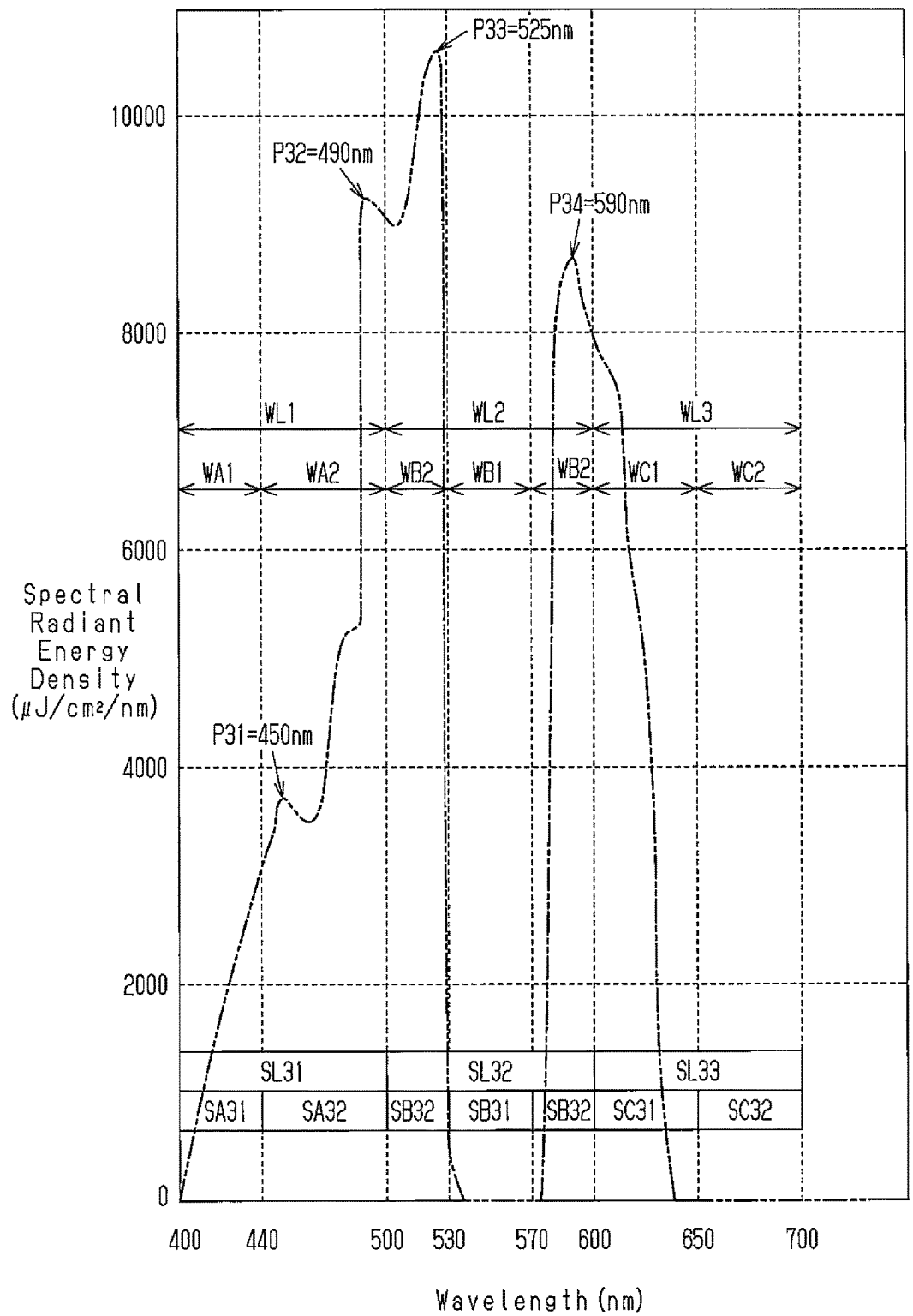
FIG. 7 is a graph partially showing the spectrum of cosmetic light for body hair applied from the optical cosmetic device for body hair in the third embodiment.

The inventors of the present application have identified the wavelength of cosmetic light for body hair that can reduce the side effects and improve the cosmetic treatment effect. The solid lines in FIGS. 4 and 5 show the spectrum of cosmetic light for body hair applied from the optical cosmetic device for body hair according to the first embodiment. The broken lines in FIGS. 4 and 6 show the spectrum of cosmetic light for body hair applied from the optical cosmetic device for body hair according to the second embodiment. The double-dashed lines in FIGS. 4 and 7 show the spectrum of cosmetic light for body hair applied from the optical cosmetic device for body hair in the third embodiment. In the present embodiment, the cosmetic light for body hair is light that is emitted from the light source 34 and passes through the lens 36 and the optical filter 37.

The inventors of the present application have studied the absorbance spectrum of oxyhemoglobin as well as the absorbance rate of melanin, and defined cosmetic light for body hair based on the findings. The matters studied by the inventors to define the cosmetic light for body hair and the findings will now be described.

Figure 2:
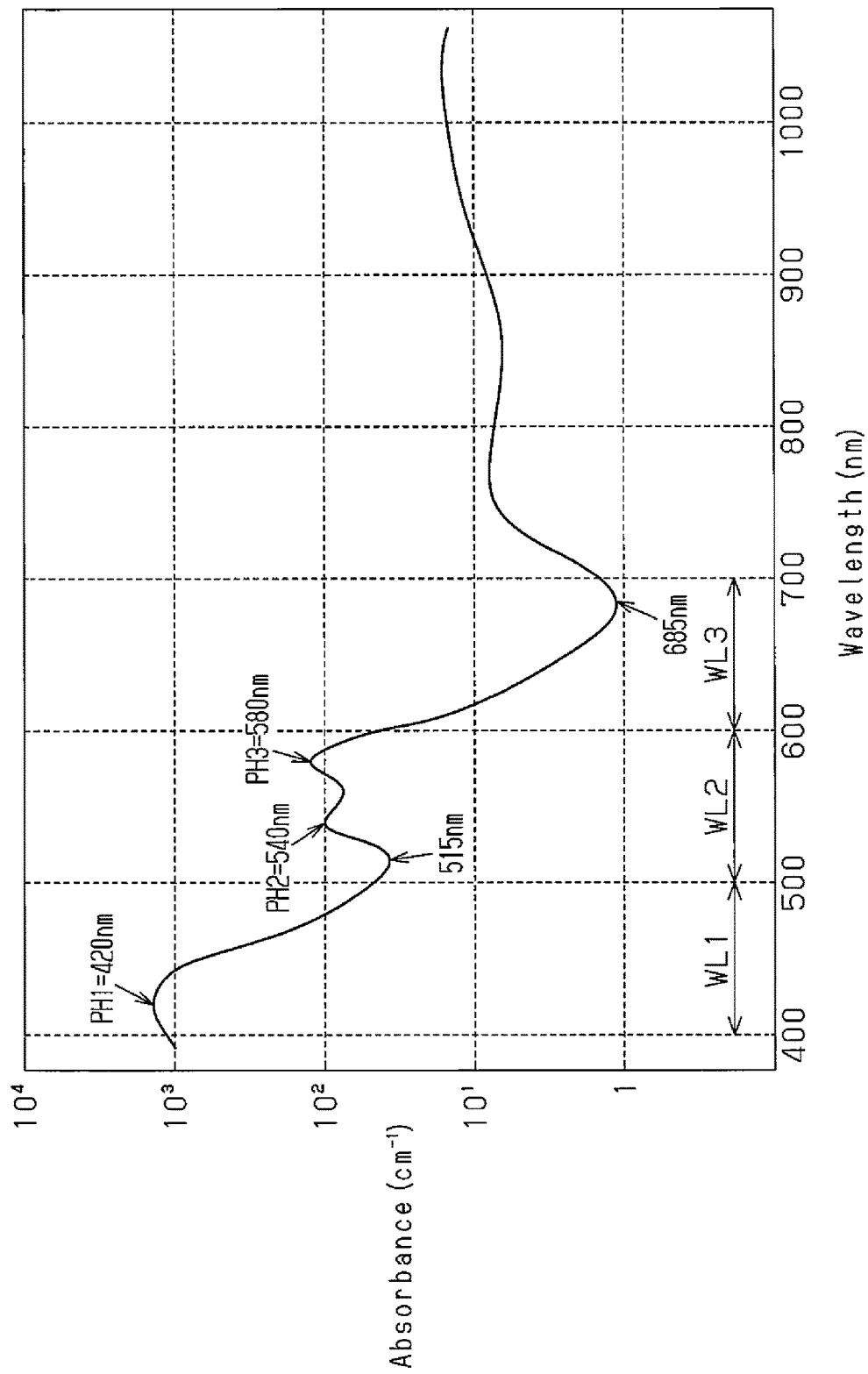
FIG. 2 is a graph showing the absorbance spectrum of oxyhemoglobin.

FIG. 2 shows the absorbance spectrum of oxyhemoglobin. Oxyhemoglobin has three absorbance peaks PH1, PH2, and PH3 in a wavelength range of 400 to 700 nm.

The first absorbance peak PH1 appears within a wavelength range of 400 to 440 nm, and has a wavelength of, for example, 420 nm. The second absorbance peak PH2 appears in a wavelength range of 530 to 570 nm, and has a wavelength of, for example, 540 nm. The third absorbance peak PH3 appears in a wavelength range of 560 to 600 nm, and has a wavelength of, for example, 580 nm.

The inventors of the present application have divided the wavelength range of 400 to 700 nm into three, and determined the integral of the absorbance of oxyhemoglobin (hereafter, absorbance integral) in each of the three wavelength ranges. The three wavelength ranges are a first wavelength range WL1, a second wavelength range WL2, and a third wavelength range WL3. The first wavelength range WL1 is a wavelength range of 400 to 500 nm. The second wavelength range WL2 is a wavelength range of 500 to 600 nm. The third wavelength range WL3 is a wavelength range of 600 to 700 nm.

The spectrum of oxyhemoglobin includes a first absorbance integral SH1 in the first wavelength range WL1, a second absorbance integral SH2 in the second wavelength range WL2, and a third absorbance integral SH3 in the third wavelength range WL3. The first absorbance integral SH1 is the largest of the three absorbance integrals. The second absorbance integral SH2 is the intermediate of the three absorbance integrals. The third absorbance integral SH3 is the smallest of the three absorbance integrals.

The inventors of the present application obtained the findings described below from the relationship between the three absorbance integrals.

Light in the first wavelength range WL1 is more easily absorbed by oxyhemoglobin than light in the second wavelength range WL2 and light in the third wavelength range WL3. A living body can have unwanted side effects on its skin when the oxyhemoglobin absorbs light. Thus, light in the first wavelength range WL1 is more likely to cause unwanted side effects on the skin than light in the second wavelength range WL2 and light in the third wavelength range WL3. To reduce unwanted side effects on the skin, it is preferable to set the amount of light energy in the first wavelength range WL1 to be less than the amounts of light energy in the second wavelength range WL2 and the third wavelength range WL3.

The body hair contains at least one of two pigments, namely, eumelanin and pheomelanin. Eumelanin is black-brown. Pheomelanin is orange-red. The color of the body hair changes in accordance with the ratio of eumelanin and pheomelanin (hereafter, melanin ratio).

Hair can be classified into one of four types depending on its color. The four types of hair are black hair, chestnut hair, blond hair, and red hair. The four types of hair differ from one another in the contents of the two pigments. Black hair has the highest content of eumelanin, and the lowest content of pheomelanin. Black hair has a high content of eumelanin, and has no or almost no content of pheomelanin. Chestnut hair has the second largest content of eumelanin, and the second lowest content of pheomelanin. Blond hair has the second lowest content of eumelanin, and the second highest content of pheomelanin. Red hair has the lowest content of eumelanin, and the highest content of pheomelanin. Chestnut hair, blond hair, and red hair each have a high content of pheomelanin.

Figure 3:
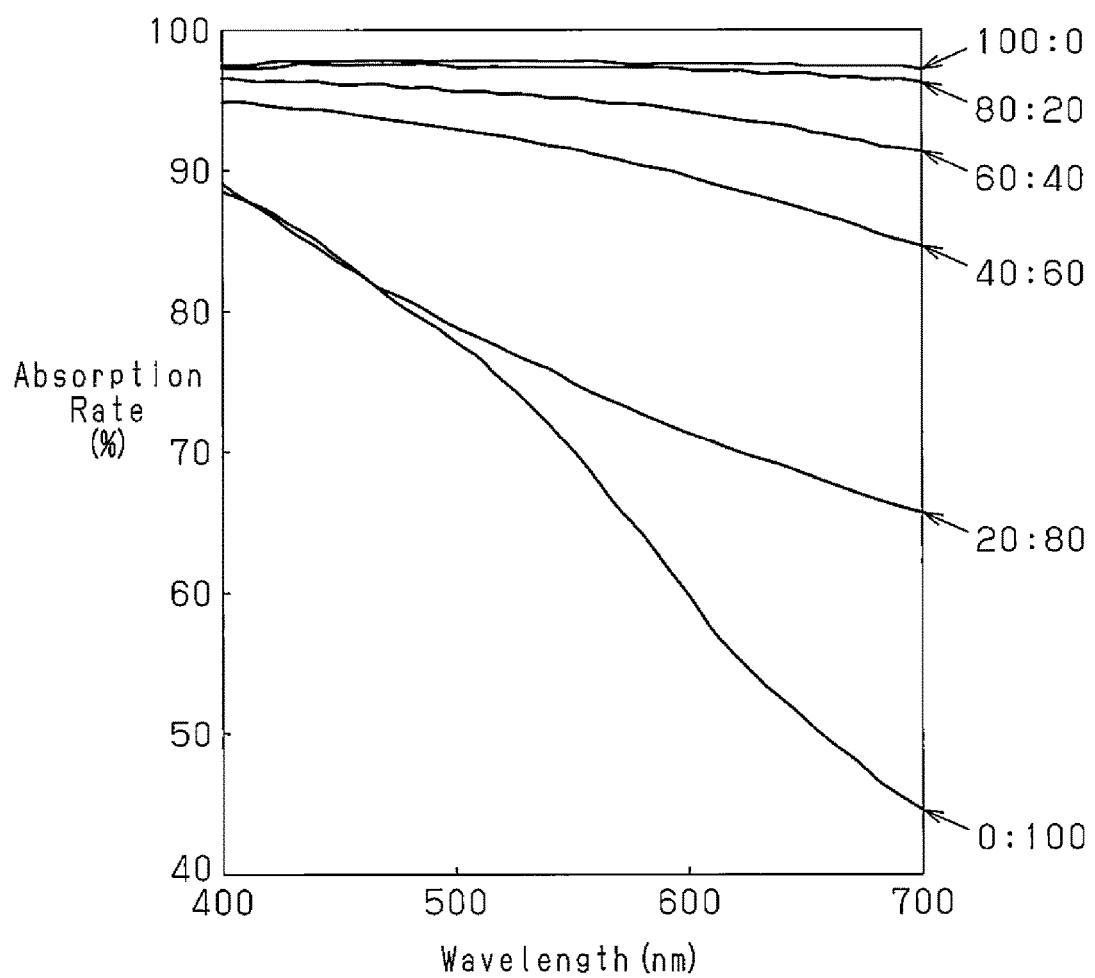
FIG. 3 is a graph illustrating absorbance in different types of body hair.

The inventors of the present application have studied the absorbance rate of body hair samples that vary in the melanin ratio. The curves in FIG. 3 show the experimental results for the body hair samples with the melanin ratios of 100:0, 80:20, 60:40, 40:60, 20:80, and 0:100 in the order from the top. The absorbance rate can be determined with a measurement method for the absorbance. For example, the absorption rate of body hair can be measured by using a spectrophotometer.

The graph of FIG. 3 shows that the absorbance rate of eumelanin is greater than the absorbance rate of pheomelanin. The absorbance rate of eumelanin is less susceptible to the influence of a wavelength of 400 to 700 nm. The absorbance rate of eumelanin is substantially uniform in the wavelength range of 400 to 700 nm.

The absorbance rate of pheomelanin is more susceptible to the influence of a wavelength of 400 to 700 nm than eumelanin. The absorbance rate of pheomelanin decreases greatly as the wavelength increases in the range of 400 to 700 nm. The absorbance rate of pheomelanin at a wavelength of 700 nm is about one-half the absorbance rate at a wavelength of 400 nm.

The absorbance rate of body hair changes in accordance with the melanin ratio in the wavelength range of 400 to 700 nm. The absorbance rate of body hair decreases as the ratio of pheomelanin increases in the wavelength range of 400 to 700 nm. The absorbance rate of body hair is less susceptible to the influence of a wavelength as the ratio of eumelanin increases. The absorbance rate of body hair is more susceptible to the influence of a wavelength as the ratio of pheomelanin increases. The absorbance rate of body hair decreases as the wavelength increases. The absorbance rate of body hair increases in accordance with the longer wavelength by a greater degree as the ratio of pheomelanin increases.

The cosmetic treatment effect of body hair differs in accordance with the amount of light energy absorbed by melanin of body hair. The cosmetic treatment effect of body hair is more likely to be improved as the amount of light energy absorbed by melanin increases. Light with a long wavelength is less easily absorbed by pheomelanin. Thus, light with a long wavelength is less likely to improve the cosmetic treatment effect of body hair having a high content of pheomelanin.

The inventors of the present application have summarized the above experimental results for oxyhemoglobin and melanin and other information, and determined the relationship between the spectrum of cosmetic light for body hair and the side effects reduction as well as the improvement in the cosmetic treatment effect.

The unwanted side effects on the skin correlate with the amount of light energy absorbed by oxyhemoglobin. The unwanted side effects on the skin are more likely to increase as the amount of light energy absorbed by oxyhemoglobin increases. Light in a wavelength range of 400 to 500 nm is more easily absorbed by oxyhemoglobin than light in a wavelength of 500 to 600 nm and light in a wavelength range of 600 to 700 nm. To mainly reduce unwanted side effects on the skin, it is preferable that light with a shorter wavelength within the wavelength range of 400 to 700 nm has a smaller amount of light energy.

The cosmetic treatment effect of body hair is correlated with the amount of light energy absorbed by melanin. The cosmetic treatment effect of body hair is improved as the amount of light energy absorbed by melanin of body hair increases. Melanin of body hair is more likely to absorb light in the wavelength range of 400 to 700 nm as the wavelength of the irradiation light decreases. To mainly improve the cosmetic treatment effect of body hair, it is preferable that light with a shorter wavelength within the wavelength range of 400 to 700 nm has a larger amount of light energy.

The above facts indicate the following. The light irradiating the body hair is less likely to cause unwanted side effects on the skin when the amount of light energy within the wavelength range of 400 to 500 nm is small. However, the amount of light energy absorbed by melanin decreases. This increases the likelihood that the cosmetic treatment effect of body hair may not be improved. The light irradiating the body hair is more likely to improve the cosmetic treatment effect of body hair when the amount of light energy within the wavelength range of 400 to 500 nm is large. However, the amount of light energy absorbed by oxyhemoglobin increases. This increases the likelihood of unwanted side effects on the skin.

Based on these findings, the inventors of the present application have identified cosmetic light for body hair that achieves a proper balance between the amount of light energy absorbed by oxyhemoglobin and the amount of light energy absorbed by melanin. Such cosmetic light for body hair reduces the side effects and improves the cosmetic treatment effect. The cosmetic light for body hair is defined by the relationship between the amount of light energy in the wavelength range of 400 to 500 nm and the amount of light energy in the wavelength range of 500 to 600 nm. The cosmetic light for body hair has a smaller amount of light energy in the wavelength range of 400 to 500 nm than in the wavelength range of 500 to 600 nm. The amount of light energy can be defined by the intensity integral in the wavelength range of 400 to 500 nm and the intensity integral in the wavelength range of 500 to 600 nm.

The cosmetic light for body hair has a smaller amount of light energy in the wavelength range of 400 to 500 nm than in the wavelength range of 500 to 600 nm. Such cosmetic light is less easily absorbed by oxyhemoglobin and is less likely to cause unwanted side effects on the skin. The cosmetic light for body hair has a preferable amount of light energy in the wavelength range of 400 to 700 nm. Thus, the cosmetic light for body hair is likely to improve the cosmetic treatment effect of body hair.

The cosmetic light for body hair can reduce the side effects independently from the relationship between the amount of light energy in the wavelength range of 400 to 500 nm and the amount of light energy in the wavelength range of 600 to 700 nm. One example of the cosmetic light for body hair can have an optical spectrum focusing on reducing the side effects. Such cosmetic light for body hair has a smaller amount of light energy in the wavelength range of 400 to 500 nm than in the wavelength range of 600 to 700 nm. Another example of the cosmetic light for body hair has an optical spectrum focusing on improving the cosmetic treatment effect. Such cosmetic light for body hair has a larger amount of light energy in the wavelength range of 400 to 500 nm than in the wavelength range of 600 to 700 nm.

As described above, the optical cosmetic device 10 for body hair has novel characteristics. The first novel characteristic is in that the optical cosmetic device 10 determines the optical spectrum of light based on both the influence of light on oxyhemoglobin of body hair and the influence of light on melanin of body hair to achieve a proper balance between the influence of light on oxyhemoglobin and the influence of light on melanin. The second novel characteristic is in that the optical cosmetic device 10 determines the spectrum of cosmetic light for body hair based on the relationship between the integrals of the light intensities in the several predetermined wavelength ranges.

The spectrum of cosmetic light for body hair will now be described. The intensity of the cosmetic light for body hair is defined by, for example, the spectral radiant energy density ($\mu J/cm^2/nm$). The cosmetic light for body hair has a larger intensity integral in the wavelength range of 400 to 700 nm than in the wavelength range of 700 to 1200 nm. The cosmetic light for body hair has a significant light intensity peak in the wavelength range of 400 to 700 nm, and has no significant light intensity peak in a wavelength range longer than 700 nm. The cosmetic light for body hair having a significant peak may be referred to as the cosmetic light having a peak. The cosmetic light for body hair having no significant light intensity peak may be referred to as the cosmetic light having no peak.

The cosmetic light for body hair can be divided into a wavelength component having an energy density not less than a predetermined spectral radiant energy density, and a wavelength component having an energy density less than the predetermined spectral radiant energy density. The wavelength component having an energy density not less than the predetermined spectral radiant energy density is understood to have a significant influence on the growth of body hair. The wavelength component having an energy density less than the predetermined spectral radiant energy density is understood to have no significant influence on the growth of body hair. The significant peak of the cosmetic light for body hair is a peak appearing for the wavelength component having an energy density not less than the predetermined spectral radiant energy density. In the graphs of FIGS. 4 to 7, the wavelength component at 0 has an energy density less than the predetermined spectral radiant energy density.

The cosmetic light for body hair has the characteristic spectrum shown in FIG. 5.

In FIG. 5, the first wavelength range WL1 is divided into a low wavelength range WA1 and a high wavelength range WA2. The low wavelength range WA1 is a wavelength range of 400 to 440 nm. The first wavelength range WL1 corresponds to a wavelength range in which the first absorbance peak PH1 of oxyhemoglobin appears (refer to FIG. 2). The high wavelength range WA2 is a wavelength range obtained by eliminating the low wavelength range WA1 from the first wavelength range WL1.

The second wavelength range WL2 is divided into a second absorbance peak range WB1 and a non-second absorbance peak range WB2. The second absorbance peak range WB1 is a wavelength range of 530 to 570 nm, and corresponds to a wavelength range in which the second absorbance peak PH2 of oxyhemoglobin appears (refer to FIG. 2). The non-second absorbance peak range WB2 is a wavelength range obtained by eliminating the second absorbance peak range WB1 from the second wavelength range WL2.

The third wavelength range WL3 is divided into a high intensity wavelength range WC1 and a low intensity wavelength range WC2. The high intensity wavelength range WC1, which is included in the third wavelength range WL3, is a range containing a larger amount of light energy, and is, for example, a wavelength range of 600 to 650 nm. The low intensity wavelength range WC2, which is included in the third wavelength range WL3, is a range containing a smaller amount of light energy, and is, for example, a wavelength range of 650 to 700 nm.

The cosmetic light for body hair has three light intensity peaks P11, P12, and P13 within the wavelength range of 400 to 700 nm. The three light intensity peaks are a first peak P11, a second peak P12, and a third peak P13. The first and second peaks P11 and P12 are in the first wavelength range WL1, and the third peak P13 is in the second wavelength range WL2. The cosmetic light for body hair has no peaks in the third wavelength range WL3.

The first peak P11, which is included in the first wavelength range WL1, is, for example, in a wavelength range of 440 to 460 nm. The first peak P11 has a wavelength of, for example, 445 nm.

The first peak P11 has the smallest intensity of the peaks included in the first wavelength range WL1. The first peak P11 has the smallest intensity of the peaks included in the first wavelength range WL1 and the second wavelength range WL2. The first peak P11 has the smallest intensity of the peaks included in the first to third wavelength ranges WL1 to WL3.

The spectral radiant energy density of the first peak P11 is preferably within a first optimum energy density range. The first optimum energy density range is a preferable range for reducing the side effects and improving the cosmetic treatment effect. The first optimum energy density range is 400 to 3000 ($\mu J/cm^2/nm$) in one example, and is 200 to 1500 ($\mu J/cm^2/nm$) in another example.

The second peak P12 is, for example, in a wavelength range of 480 to 500 nm included in the first wavelength range WL1. The second peak P12 has a wavelength of, for example, 490 nm. The second peak P12 has a higher intensity than the first peak P11. The second peak P12 can have an intensity of at least twice the intensity of the first peak P11.

The second peak P12 has the largest intensity in the first wavelength range WL1. The second peak P12 has the largest intensity of the peaks included in the first wavelength range WL1. The second peak P12 has the second largest intensity of the peaks included in the first wavelength range WL1 and the second wavelength range WL2. The second peak P12 has the second largest intensity of the peaks included in the first to third wavelength ranges WL1 to WL3.

The spectral radiant energy density of the second peak P12 preferably falls within a second optimum energy density range. The second optimum energy density range is a preferable range for reducing the side effects and improving the cosmetic treatment effect. The second optimum energy density range is 933 to 7000 ($\mu J/cm^2/nm$) in one example, and is 467 to 3500 ($\mu J/cm^2/nm$) in another example.

The third peak P13 is, for example, in a wavelength range of 520 to 540 nm included in the second wavelength range WL2. The third peak P13 has a wavelength of, for example, 530 nm. The third peak P13 has a higher intensity than the first peak P11 and the second peak P12. The third peak P13 can have an intensity of at least twice the intensity of the first peak P11.

The third peak P13 has the largest intensity in the second wavelength range WL2. The third peak P13 has the largest intensity of the peaks included in the first wavelength range WL1 and the second wavelength range WL2. The third peak P13 has the largest intensity of the peaks included in the first to third wavelength ranges WL1 to WL3.

The spectral radiant energy density of the third peak P13 preferably falls within a third optimum energy density range. The third optimum energy density range is a preferable range for reducing the side effects and improving the cosmetic treatment effect. The third optimum energy density range is 1040 to 7800 ($\mu J/cm^2/nm$) in one example, and is 1307 to 9800 ($\mu J/cm^2/nm$) in another example.

The cosmetic light for body hair has the largest increasing rate in the first to third wavelength ranges WL1 to WL3 that falls within the wavelength range of 480 to 500 nm. The increasing rate can be defined as the increase in the intensity per unit wavelength.

The intensity integral of cosmetic light for body hair in the first wavelength range WL1 is hereafter referred to as an integral SL11. The intensity integral of cosmetic light for body hair in the low wavelength range WA1 is referred to as an integral SA11. The intensity integral of cosmetic light for body hair in the high wavelength range WA2 is referred to as an integral SA12.

Likewise, the intensity integral of cosmetic light for body hair in the second wavelength range WL2 is an integral SL12. The intensity integral of cosmetic light for body hair in the second absorbance peak range WB1 is an integral SB11. The intensity integral of cosmetic light for body hair in the non-second absorbance peak range WB2 is an integral SB12. The intensity integral of cosmetic light for body hair in the third wavelength range WL3 is an integral SL13. The intensity integral of cosmetic light for body hair in the high intensity wavelength range WC1 is an integral SC11. The intensity integral of cosmetic light for body hair in the low intensity wavelength range WC2 is an integral SC12.

The intensity of the cosmetic light for body hair is determined in such a manner that the total of the integrals SL11, SL12, and SL13 falls within an optimum total integral range. The optimum total integral range is a preferable range for reducing the side effects and improving the cosmetic treatment effect. The optimum total integral range is 0.2 to 1.5 ($J/cm^2$) in one example, and is 0.2 to 1.5 ($J/cm^2$) in another example.

The integral SL11 preferably falls within a first optimum integral range. The first optimum integral range is a preferable range for reducing the side effects and improving the cosmetic treatment effect. The first optimum integral range is 0.05 to 0.4 ($J/cm^2$) in one example, and is 0.03 to 0.2 ($J/cm^2$) in another example.

The integral SA11 preferably falls within a second optimum integral range. The second optimum integral range is a preferable range for reducing the side effects and improving the cosmetic treatment effect. The second optimum integral range is 0.008 to 0.06 ($J/cm^2$) in one example, and is 0.004 to 0.03 ($J/cm^2$) in another example.

The integral SA12 preferably falls within a third optimum integral range. The third optimum integral range is a preferable range for reducing the side effects and improving the cosmetic treatment effect. The third optimum integral range is 0.042 to 0.34 ($J/cm^2$) in one example, and is 0.021 to 0.17 ($J/cm^2$) in another example.

The integral SL12 preferably falls within a fourth optimum integral range. The fourth optimum integral range is a preferable range for reducing the side effects and improving the cosmetic treatment effect. The fourth optimum integral range is 0.11 to 0.8 ($J/cm^2$) in one example, and is 0.13 to 1 ($J/cm^2$) in another example.

The integral SB11 preferably falls within a fifth optimum integral range. The fifth optimum integral range is a preferable range for reducing the side effects and improving the cosmetic treatment effect. The fifth optimum integral range is 0.04 to 0.3 ($J/cm^2$) in one example, and is 0.04 to 0.3 ($J/cm^2$) in another example.

The integral SB12 preferably falls within a sixth optimum integral range. The sixth optimum integral range is a preferable range for reducing the side effects and improving the cosmetic treatment effect. The sixth optimum integral range is 0.07 to 0.5 ($J/cm^2$) in one example, and is 0.09 to 0.7 ($J/cm^2$) in another example.

The integral SL13 preferably falls within a seventh optimum integral range. The seventh optimum integral range is a preferable range for reducing the side effects and improving the cosmetic treatment effect. The seventh optimum integral range is 0.04 to 0.3 ($J/cm^2$) in one example, and is 0.04 to 0.3 ($J/cm^2$) in another example.

The integral SC11 preferably falls within an eighth optimum integral range. The eighth optimum integral range is a preferable range for reducing the side effects and improving the cosmetic treatment effect. The eighth optimum integral range is 0.04 to 0.3 ($J/cm^2$) in one example, and is 0.04 to 0.3 ($J/cm^2$) in another example.

The integral SC12 preferably falls within a ninth optimum integral range. The ninth optimum integral range is a preferable range for reducing the side effects and improving the cosmetic treatment effect. The ninth optimum integral range is, for example, 0 ($J/cm^2$).

The intensity integrals have the relationship described below at the optical spectrum shown in FIG. 5.
 (a) The integral SL11 is smaller than the integral SL12.
 (b) The integral SL11 is larger than the integral SL13.
 (c) The integral SA11 is smaller than the integral SA12.
 (d) The integral SB11 is smaller than the integral SB12.
 (e) The integral SC11 is larger than the integral SC12.
 (f) The integral SA11 is smaller than the integral SB11.
 (g) The integral SA11 is smaller than the integral SB12.
 (h) The integral SA11 is smaller than the integral SC11.
 (i) The integral SA11 is larger than the integral SC12.

(j) The integral SA12 is larger than the integral SB11.
(k) The integral SA12 is smaller than the integral SB12.
(l) The integral SA12 is larger than the integral SC11.
(m) The integral SA12 is larger than the integral SC12.
(n) The integral SB11 is larger than the integral SC11.
(o) The integral SB11 is larger than the integral SC12.
(p) The integral SB12 is larger than the integral SC11.
(q) The integral SB12 is larger than the integral SC12.

The present embodiment has the advantages described below.

(1) The optical cosmetic device 10 for body hair emits the cosmetic light for body hair. The cosmetic light for body hair has a larger intensity integral in the wavelength range of 400 to 700 nm than in the wavelength range of 700 to 1200 nm. The inventors of the present application have determined through experiments that the characteristic cosmetic light for body hair has the following advantage. The cosmetic light for body hair has a large amount of light energy absorbed by melanin, and thus is likely to improve the cosmetic treatment effect of body hair. The optical cosmetic device 10 for body hair thus can inhibit the growth of body hair.

(2) The cosmetic light for body hair has a smaller intensity integral in the wavelength range of 400 to 500 nm than in the wavelength range of 500 to 600 nm. The inventors of the present application have determined through experiments that the characteristic cosmetic light for body hair has the following advantage. The cosmetic light for body hair has a smaller amount of light energy absorbed by oxyhemoglobin than when the intensity integral is larger in the wavelength range of 400 to 500 nm than in the wavelength range of 500 to 600 nm. The optical cosmetic device 10 for body hair thus is less likely to cause unwanted side effects on the skin.

(3) The optical cosmetic device 10 for body hair has advantages (1) and (2) in combination. In other words, the optical cosmetic device 10 for body hair is less likely to cause unwanted side effects on the skin and can inhibit the growth of body hair.

(4) The cosmetic light for body hair has a larger intensity integral in the wavelength range of 500 to 600 nm than in the wavelength range of 600 to 700 nm. The inventors of the present application have determined through experiments that the characteristic cosmetic light for body hair has the following advantage. The cosmetic light for body hair has a larger amount of light energy absorbed by melanin in the wavelength range of 500 to 600 nm than in the wavelength range of 600 to 700 nm. The optical cosmetic device 10 for body hair thus improves the cosmetic treatment effect of body hair.

(5) The cosmetic light for body hair has a larger intensity integral in the wavelength range of 500 to 600 nm than in the wavelength range of 600 to 700 nm. The inventors of the present application have determined through experiments that the characteristic cosmetic light for body hair has the following advantage. The light having a wavelength of 500 to 600 nm has a larger influence on pheomelanin than the light having a wavelength longer than 600 nm. Thus, the cosmetic light for body hair has a larger amount of light energy absorbed by pheomelanin than when the intensity integral is smaller in the wavelength range of 500 to 600 nm than in the wavelength range of 600 to 700 nm. This prevents the cosmetic treatment effect of body hair from deteriorating when the body hair has a high content of pheomelanin.

(6) The optical cosmetic device 10 for body hair has advantages (2) and (5) above in combination. In other words, the optical cosmetic device 10 improves the cosmetic treatment effect of body hair having a high content of pheomelanin and lowers the likelihood of causing unwanted side effects on the skin. The optical cosmetic device 10 for body hair has a small negative effect on the skin of a living body with chestnut hair, blond hair, or red hair, and improves the cosmetic treatment effect on the body hair.

(7) The cosmetic light for body hair has a larger intensity integral in the wavelength range of 400 to 500 nm than in the wavelength range of 600 to 700 nm. The inventors of the present application have determined through experiments that the characteristic cosmetic light for body hair has the following advantage. The cosmetic light for body hair achieves a higher body hair cosmetic treatment effect than when the intensity integral is smaller in the wavelength range of 400 to 500 nm than in the wavelength range of 600 to 700 nm.

(8) The cosmetic light for body hair has a larger integral in the wavelength range of 500 to 530 nm than in the wavelength range of 570 to 600 nm. The inventors of the present application have determined through experiments that the characteristic cosmetic light for body hair has the following advantage. The cosmetic light for body hair achieves a higher body hair cosmetic treatment effect than when the intensity integral is larger in the wavelength range of 500 to 530 nm than in the wavelength range of 570 to 600 nm.

(9) The cosmetic light for body hair has the first peak P11 in the wavelength range of 440 to 460 nm. The first peak P11 has the smallest value of the peaks included in the wavelength range of 400 to 700 nm. The inventors of the present application have determined through experiments that the characteristic cosmetic light for body hair has the following advantage. The cosmetic light for body hair is less likely to cause unwanted side effects on the skin than when the first peak P11 is larger than other peaks included in the wavelength range of 400 to 700 nm.

(10) The cosmetic light for body hair has the first peak P11 in the wavelength range of 440 to 460 nm. The first peak P11 has the smallest value of the peaks included in the wavelength range of 400 to 600 nm. The inventors of the present application have determined through experiments that the characteristic cosmetic light for body hair has the following advantage. The cosmetic light for body hair is less likely to cause unwanted side effects on the skin than when the first peak P11 is larger than other peaks included in the wavelength range of 400 to 600 nm.

(11) The cosmetic light for body hair has the second peak P12 in the wavelength range of 480 to 500 nm. The second peak P12 has the second largest value of the peaks included in the wavelength range of 400 to 700 nm. The inventors of the present application have determined through experiments that the characteristic cosmetic light for body hair has the following advantage. The cosmetic light for body hair achieves a higher body hair cosmetic treatment effect than when the second peak P12 is a value that is smaller than or equal to the third largest value of the peaks included in the wavelength range of 400 to 700 nm.

(12) The cosmetic light for body hair has the second peak P12 in the wavelength range of 480 to 500 nm. The second peak P12 has the second largest value of the peaks included in the wavelength range of 400 to 600 nm. The inventors of the present application have determined through experiments that the characteristic cosmetic light for body hair has the following advantage. The cosmetic light for body hair achieves a higher body hair cosmetic treatment effect than when the second peak P12 is a value that is smaller than or equal to the third largest value of the peaks included in the wavelength range of 400 to 600 nm.

(13) The cosmetic light for body hair has the first peak P11 in the wavelength range of 440 to 460 nm. The cosmetic light for body hair has the second peak P12 in the wavelength range of 480 to 500 nm. The second peak P12 has an intensity of at least twice the intensity of the first peak P11. The inventors of the present application have determined through experiments that the characteristic cosmetic light for body hair has the following advantage. The cosmetic light for body hair achieves a higher body hair cosmetic treatment effect than when the second peak P12 has a smaller intensity than twice the intensity of the first peak P11.

(14) The cosmetic light for body hair has the third peak P13 in the wavelength range of 520 to 540 nm. The third peak P13 has the largest value of the peaks included in the wavelength range of 400 to 700 nm. The inventors of the present application have determined through experiments that the characteristic cosmetic light for body hair has the following advantage. The cosmetic light for body hair achieves a higher body hair cosmetic treatment effect than when the third peak P13 is a value that is smaller than or equal to the second largest value of the peaks included in the wavelength range of 400 to 700 nm.

(15) The cosmetic light for body hair has the third peak P13 in the wavelength range of 520 to 540 nm. The third peak P13 has the maximum value of the peaks included in the wavelength range of 400 to 600 nm. The inventors of the present application have determined through experiments that the characteristic cosmetic light for body hair has the following advantage. The cosmetic light for body hair achieves a higher body hair cosmetic treatment effect than when the third peak P13 is a value that is smaller than or equal to the second largest value of the peaks included in the wavelength range of 400 to 600 nm.

(16) The cosmetic light for body hair has the first peak P11 in the wavelength range of 440 to 460 nm. The cosmetic light for body hair has the third peak P13 in the wavelength range of 520 to 540 nm. The third peak P13 has an intensity of at least twice the intensity of the first peak P11. The inventors of the present application have determined through experiments that the characteristic cosmetic light for body hair has the following advantage. The cosmetic light for body hair achieves a higher body hair cosmetic treatment effect than when the third peak P13 has a smaller intensity than twice the intensity of the first peak P11.

(17) The cosmetic light for body hair has the first peak P11 in the wavelength range of 440 to 460 nm. The inventors of the present application have determined through experiments that the characteristic cosmetic light for body hair has the following advantage. The cosmetic light for body hair is more preferable for reducing the side effects and improving the cosmetic treatment effect than when the first peak P11 is outside the wavelength range of 440 to 460 nm.

(18) The cosmetic light for body hair has the second peak P12 in the wavelength range of 480 to 500 nm. The inventors of the present application have determined through experiments that the characteristic cosmetic light for body hair has the following advantage. The cosmetic light for body hair is more preferable for reducing the side effects and improving the cosmetic treatment effect than when the second peak P12 is outside the wavelength range of 480 to 500 nm.

(19) The cosmetic light for body hair has the third peak P13 in the wavelength range of 520 to 540 nm. The inventors of the present application have determined through experiments that the characteristic cosmetic light for body hair has the following advantage. The cosmetic light for body hair is more preferable for reducing the side effects and improving the cosmetic treatment effect than when the third peak P13 is outside the wavelength range of 520 to 540 nm.

(20) The cosmetic light for body hair has the largest increasing rate for the wavelength range of 400 to 700 nm that falls within the wavelength range of 480 to 500 nm. The inventors of the present application have determined through experiments that the characteristic cosmetic light for body hair has the following advantage. The cosmetic light for body hair achieves a higher body hair cosmetic treatment effect than when the light having the largest increasing rate is in a wavelength range shorter than the wavelength range of 480 to 500 nm.

(21) The cosmetic light for body hair has an energy density in the range of 0.2 to 1.5 ($J/cm^2$). The inventors of the present application have determined through experiments that the characteristic cosmetic light for body hair has the following advantage. The cosmetic light for body hair achieves a higher body hair cosmetic treatment effect than the light having an energy density less than 0.2 ($J/cm^2$). The cosmetic light for body hair is less likely to cause unwanted side effects on the skin than the light having an energy density that is greater than 1.5 ($J/cm^2$).

(22) The cosmetic light for body hair has an irradiation time per irradiation in the range of 600 µs to 2 ms. The inventors of the present application have determined through experiments that the characteristic cosmetic light for body hair has the following advantage. The cosmetic light for body hair achieves a higher body hair cosmetic treatment effect than when the irradiation time is shorter than 600 µs. The cosmetic light for body hair is less likely to cause unwanted side effects on the skin than when the irradiation time is longer than 2 ms.

Second Embodiment

A second embodiment of the optical cosmetic device 10 differs from the device of the first embodiment in that it uses cosmetic light for body hair having optical spectra indicated by the broken lines in FIGS. 4 and 6.

The cosmetic light for body hair according to the second embodiment has three peaks P21, P22, P23 in a wavelength range of 400 to 700 nm. The first peak P21 and the second peak P22 are in a first wavelength range WL1. The third peak P23 is in a second wavelength range WL2. The cosmetic light for body hair has no peaks in a third wavelength range WL3.

The first peak P21 falls in the first wavelength range WL1 and is, for example, in a wavelength range of 450 to 470 nm. The first peak P21 has a wavelength of, for example, 460 nm.

The first peak P21 has the smallest intensity of the peaks included in the first wavelength range WL1. The first peak P21 has the smallest intensity of the peaks included in the first wavelength range WL1 and the second wavelength range WL2. The first peak P21 has the smallest intensity of the peaks included in the first to third wavelength ranges WL1 to WL3.

The first peak P21 preferably falls within a first optimum energy density range. The first optimum energy density range is a preferable range for reducing the side effects and improving the cosmetic treatment effect. The first optimal energy density range is 400 to 3000 ($J/cm^2$) in one example, and is 200 to 1500 ($J/cm^2$) in another example.

The second peak P22 falls in the first wavelength range WL1 and is, for example, in a wavelength range of 480 to 500 nm. The second peak P22 has a wavelength of, for example, 490 nm. The second peak P22 has a higher intensity than the first peak P21. The second peak P22 has an intensity of at least twice the intensity of the first peak P21.

The second peak P22 has the largest intensity in the first wavelength range WL1. The second peak P22 has the largest intensity of the peaks included in the first wavelength range WL1. The second peak P22 has the second largest intensity of the peaks included in the first wavelength range WL1 and the second wavelength range WL2. The second peak P22 has the second largest intensity of the peaks included in the first to third wavelength ranges WL1 to WL3.

The second peak P22 preferably falls within a second optimum energy density range. The second optimum energy density range is a preferable range for reducing the side effects and improving the cosmetic treatment effect. The second optimum energy range is 1000 to 7500 ($\mu$J/cm$^2$/nm) in one example, and is 500 to 3750 (J/cm$^2$) in another example.

The third peak P23 is formed in the second wavelength range WL2 and is, for example, in a wavelength range of 520 to 540 nm. The third peak P23 has a wavelength of, for example, 530 nm. The third peak P23 has a higher intensity than the first peak P21 and the second peak P22. The third peak P23 has an intensity of at least twice the intensity of the first peak P21.

The third peak P23 has the largest intensity in the second wavelength range WL2. The third peak P23 has the largest intensity of the peaks included in the first wavelength range WL1 and the second wavelength range WL2. The third peak P23 has the largest intensity of the peaks included in the first to third wavelength ranges WL1 to WL3.

The third peak P23 preferably falls within a third optimum energy density range. The third optimum energy density range is a preferable range for reducing the side effects and improving the cosmetic treatment effect. The third optimum energy density range is, for example, 1093 to 8200 ($\mu$J/cm$^2$/nm) in one example, and is 1307 to 9800 ($\mu$J/cm$^2$/nm) in another example.

In the first to third wavelength ranges WL1 to WL3, the cosmetic light for body hair has the largest increasing rate in the wavelength range of 480 to 500 nm. The increasing rate can be defined as the increasing rate in the intensity per unit wavelength.

The light intensity integral in the first wavelength range WL1 is referred to as an integral SL21. The light intensity integral in the low wavelength range WA1 is referred to as an integral SA21. The light intensity integral in the high wavelength range WA2 is referred to as an integral SA22.

Likewise, the light intensity integral in the second wavelength range WL2 is an integral SL22. The light intensity integral in the second absorbance peak range WB1 is an integral SB21. The light intensity integral in the non-second absorbance peak range WB2 is an integral SB22. The light intensity integral in the third wavelength range WL3 is an integral SL23. The light intensity integral in the high intensity wavelength range WC1 is an integral SC21. The light intensity integral in the low intensity wavelength range WC2 is an integral SC22.

The intensity of the cosmetic light for body hair is set in such a manner that the total of the integrals SL21, SL22, and SL23 will fall within an optimum total integral range. The optimum total integral range is a preferable range for reducing the side effects and improving the cosmetic treatment effect. The optimum total integral range is 0.2 to 1.5 (J/cm$^2$) in one example, and is 0.2 to 1.5 (J/cm$^2$) in another example.

The integral SL21 preferably falls within a first optimum integral range. The first optimum integral range is a preferable range for reducing the side effects and improving the cosmetic treatment effect. The first optimum integral range is 0.04 to 0.3 (J/cm$^2$) in one example, and is 0.03 to 0.2 (J/cm$^2$) in another example.

The integral SA21 preferably falls within a second optimum integral range. The second optimum integral range is a preferable range for reducing the side effects and improving the cosmetic treatment effect. The second optimum integral range is 0.003 to 0.02 (J/cm$^2$) in one example, and is 0 (J/cm$^2$) in another example.

The integral SA22 preferably falls within a third optimum integral range. The third optimum integral range is a preferable range for reducing the side effects and improving the cosmetic treatment effect. The third optimum integral range is 0.037 to 0.28 (J/cm$^2$) in one example, and is 0.03 to 0.2 (J/cm$^2$) in another example.

The integral SL22 preferably falls within a fourth optimum integral range. The fourth optimum integral range is a preferable range for reducing the side effects and improving the cosmetic treatment effect. The fourth optimum integral range is 0.12 to 0.9 (J/cm$^2$) in one example, and is 0.13 to 1 (J/cm$^2$) in another example.

The integral SB21 preferably falls within a fifth optimum integral range. The fifth optimum integral range is a preferable range for reducing the side effects and improving the cosmetic treatment effect. The fifth optimum integral range is 0.045 to 0.34 (J/cm$^2$) in one example, and is 0.04 to 0.3 (J/cm$^2$) in another example.

The integral SB22 preferably falls within a sixth optimum integral range. The sixth optimum integral range is a preferable range for reducing the side effects and improving the cosmetic treatment effect. The sixth optimum integral range is 0.075 to 0.56 (J/cm$^2$) in one example, and is 0.09 to 0.7 (J/cm$^2$) in another example.

The integral SL23 preferably falls within a seventh optimum integral range. The seventh optimum integral range is a preferable range for reducing the side effects and improving the cosmetic treatment effect. The seventh optimum integral range is 0.04 to 0.3 (J/cm$^2$) in one example, and is 0.04 to 0.3 (J/cm$^2$) in another example.

The integral SC21 preferably falls within an eighth optimum integral range. The eighth optimum integral range is a preferable range for reducing the side effects and improving the cosmetic treatment effect. The eighth optimum integral range is 0.04 to 0.3 (J/cm$^2$) in one example, and is 0.04 to 0.3 (J/cm$^2$) in another example.

The integral SC22 preferably falls within a ninth optimum integral range. The ninth optimum integral range is a preferable range for reducing the side effects and improving the cosmetic treatment effect. The ninth optimum integral range is 0 (J/cm$^2$) in one example.

The intensity integrals have the relationship described below at the optical spectrum shown in FIG. 6.

(a) The integral SL21 is smaller than the integral SL22.
(b) The integral SL21 is smaller than the integral SL23.
(c) The integral SA21 is smaller than the integral SA22.
(d) The integral SB21 is smaller than the integral SB22.
(e) The integral SC21 is larger than the integral SC22.
(f) The integral SA21 is smaller than the integral SB21.
(g) The integral SA21 is smaller than the integral SB22.
(h) The integral SA21 is smaller than the integral SC21.
(i) The integral SA21 is equal to the integral SC22.
(j) The integral SA22 is smaller than the integral SB21.
(k) The integral SA22 is smaller than the integral SB22.
(l) The integral SA22 is smaller than the integral SC21.

(m) The integral SA22 is larger than the integral SC22.
(n) The integral SB21 is larger than the integral SC21.
(o) The integral SB21 is larger than the integral SC22.
(p) The integral SB22 is larger than the integral SC21.
(q) The integral SB22 is larger than the integral SC22.

The optical cosmetic device 10 for body hair according to the second embodiment has the advantages equivalent to the advantages (1) to (22) produced by the optical cosmetic device 10 for body hair according to the first embodiment. More specifically, the optical cosmetic device 10 according to the second embodiment is less likely to cause unwanted side effects on the skin and is capable of inhibiting the growth of body hair, and has other various advantages. The optical cosmetic device 10 for body hair according to the second embodiment further has the advantages described below.

(23) The integral SA21 of the cosmetic light for body hair is smaller than the integral SA11. The inventors of the present application have determined through experiments that the characteristic cosmetic light for body hair has the following advantage. The cosmetic light for body hair is more likely to reduce the unwanted side effects on the skin than when the integral SA21 is larger than the integral SA11.

Third Embodiment

A third embodiment of the optical cosmetic device 10 differs from the device of the first embodiment in that it uses cosmetic light for body hair having optical spectra indicated by the double-dashed line in FIGS. 4 and 7.

The cosmetic light for body hair of the third embodiment has four peaks in a wavelength range of 400 to 700 nm. The cosmetic light for body hair has two of the four peaks in a first wavelength range WL1, and two of the four peaks in a second wavelength range WL2. The cosmetic light for body hair has no peaks in a third wavelength range WL3. The four peaks are a first peak P31, a second peak P32, a third peak P33, and a fourth peak P34.

The first peak P31 is in the first wavelength range WL1. The first peak P31 is, for example, in a wavelength range of 440 to 460 nm. The first peak P31 has a wavelength of, for example, 450 nm.

The first peak P31 has the smallest intensity of the peaks included in the first wavelength range WL1. The first peak P31 has the smallest intensity of the peaks included in first wavelength range WL1 and the second wavelength range WL2. The first peak P31 has the smallest intensity of the peaks included in first to third wavelength ranges WL1 to WL3.

The first peak P31 preferably falls within a first optimum energy density range. The first optimum energy density range is a preferable range for reducing the side effects and improving the cosmetic treatment effect. The first optimum energy range is 507 to 3800 (J/cm$^2$) in one example, and is 254 to 1900 (J/cm$^2$) in another example.

The second peak P32 is formed in the first wavelength range WL1. The second peak P32 is for example in a wavelength range of 480 to 500 nm. The second peak P32 has a wavelength of, for example, 490 nm. The second peak P32 has a higher intensity than the first peak P31. The second peak P32 has an intensity of at least twice the intensity of the first peak P31.

The second peak P32 has the largest intensity in the first wavelength range WL1. The second peak P32 has the largest intensity of the peaks included in the first wavelength range WL1. The second peak P32 has the second largest intensity of the peaks included in the first wavelength range WL1 and the second wavelength range WL2. The second peak P32 has the second largest intensity of the peaks included in the first to third wavelength ranges WL1 to WL3.

The second peak P32 preferably falls within a second optimum energy density range. The second optimum energy density range is a preferable range for reducing the side effects and improving the cosmetic treatment effect. The second optimum energy density range is 1240 to 9300 (J/cm$^2$) in one example, and is 620 to 4650 (J/cm$^2$) in another example.

The third peak P33 is formed in the second wavelength range WL2. The third peak P33 falls within a wavelength range of, for example, 515 to 535 nm. The third peak P33 has a wavelength of, for example, 525 nm. The third peak P33 has a higher intensity than the first peak P31 and the second peak P32. The third peak P33 has an intensity of at least twice the intensity of the first peak P31.

The third peak P33 has the largest intensity in the second wavelength range WL2. The third peak P33 has the largest intensity of the peaks included in the second wavelength range WL2. The third peak P33 has the largest intensity of the peaks included in the first wavelength range WL1 and the second wavelength range WL2. The third peak P33 has the largest intensity of the peaks included in the first to third wavelength ranges WL1 to WL3.

The third peak P33 preferably falls within a third optimum energy density range. The third optimum energy density range is a preferable range for reducing the side effects and improving the cosmetic treatment effect. The third optimum energy density range is 1467 to 11000 (J/cm$^2$) in one example, and is 2444 to 18333 (J/cm$^2$) in another example.

The fourth peak P34 is formed in the second wavelength range WL2. The fourth peak P34 is formed in a wavelength range of, for example, 580 to 600 nm. The fourth peak P34 has a wavelength of, for example, 590 nm. The fourth peak P34 has a higher intensity than the first peak P31. The fourth peak P34 has an intensity of at least twice the intensity of the first peak P31.

The fourth peak P34 has the second largest intensity in the second wavelength range WL2. The fourth peak P34 has the third largest intensity of the peaks included in the first wavelength range WL1 and the second wavelength range WL2. The fourth peak P34 has the third largest intensity of the peaks included in the first to third wavelength ranges WL1 to WL3.

The fourth peak P34 preferably falls within a fourth optimum energy density range. The fourth optimum energy density range is a preferable range for reducing the side effects and improving the cosmetic treatment effect. The fourth optimum energy density range is, for example, 1173 to 8800 (J/cm$^2$) in one example, and is 1956 to 14667 (J/cm$^2$) in another example.

In the first to third wavelength ranges WL1 to WL3, the cosmetic light for body hair has the largest increasing rate in the wavelength range of 480 to 500 nm. The increasing rate can be defined as the increasing rate in the intensity per unit wavelength.

The light intensity integral in the first wavelength range WL1 is referred to as an integral SL31. The light intensity integral in the low wavelength range WA1 is referred to as an integral SA31. The light intensity integral in the high wavelength range WA2 is referred to as an integral SA32.

Likewise, the light intensity integral in the second wavelength range WL2 is an integral SL32. The light intensity integral in the second absorbance peak range WB1 is an integral SB31. The light intensity integral in the non-second absorbance peak range WB2 is an integral SB32. The light intensity integral in the third wavelength range WL3 is an integral SL33. The light intensity integral in the high intensity wavelength range WC1 is an integral SC31. The light intensity integral in the low intensity wavelength range WC2 is an integral SC32.

The intensity of the cosmetic light for body hair is determined in such a manner that the total of the integrals SL31, SL32, and SL33 will fall within an optimum total integral range. The optimum total integral range is a preferable range for reducing the side effects and improving the cosmetic treatment effect. The optimum total integral range is 0.2 to 1.5 (J/cm$^2$) in one example, and is 0.2 to 1.5 (J/cm$^2$) in another example.

The integral SL31 preferably falls within a first optimum integral range. The first optimum integral range is an integral range that can reduce the side effects and improve the cosmetic treatment effect. The first optimum integral range is 0.05 to 0.4 (J/cm$^2$) in one example, and is 0.03 to 0.2 (J/cm$^2$) in another example.

The integral SA31 preferably falls within a second optimum integral range. The second optimum integral range is a preferable range for reducing the side effects and improving the cosmetic treatment effect. The second optimum integral range is 0.008 to 0.06 (J/cm$^2$) in one example, and is 0 (J/cm$^2$) in another example.

The integral SA32 preferably falls within a third optimum integral range. The third optimum integral range is a preferable range for reducing the side effects and improving the cosmetic treatment effect. The third optimum integral range is 0.042 to 0.34 (J/cm$^2$) in one example, and is 0.03 to 0.2 (J/cm$^2$) in another example.

The integral SL32 preferably falls within a fourth optimum integral range. The fourth optimum integral range is a preferable range for reducing the side effects and improving the cosmetic treatment effect. The fourth optimum integral range is 0.08 to 0.6 (J/cm$^2$) in one example, and is 0.13 to 1 (J/cm$^2$) in another example.

The integral SB31 preferably falls within a fifth optimum integral range. The fifth optimum integral range is a preferable range for reducing the side effects and improving the cosmetic treatment effect. The fifth optimum integral range is 0 (J/cm$^2$) in one example.

The integral SB32 preferably falls within a sixth optimum integral range. The sixth optimum integral range is a preferable range for reducing the side effects and improving the cosmetic treatment effect. The sixth optimum integral range is 0.08 to 0.6 (J/cm$^2$) in one example, and is 0.13 to 1 (J/cm$^2$) in another example.

The integral SL33 preferably falls within a seventh optimum integral range. The seventh optimum integral range is a preferable range for reducing the side effects and improving the cosmetic treatment effect. The seventh optimum integral range is 0.07 to 0.5 (J/cm$^2$) in one example, and is 0.04 to 0.3 (J/cm$^2$) in another example.

The integral SC31 preferably falls within an eighth optimum integral range. The eighth optimum integral range is a preferable range for reducing the side effects and improving the cosmetic treatment effect. The eighth optimum integral range is 0.07 to 0.5 (J/cm$^2$) in one example, and is 0.04 to 0.3 (J/cm$^2$) in another example.

The integral SC32 preferably falls within a ninth optimum integral range. The ninth optimum integral range is a preferable range for reducing the side effects and improving the cosmetic treatment effect. The ninth optimum integral range is 0 (J/cm$^2$) in one example.

The intensity integrals have the relationship described below at the optical spectrum shown in FIG. 7.

(a) The integral SL31 is smaller than the integral SL32.
(b) The integral SL31 is smaller than the integral SL33.
(c) The integral SA31 is smaller than the integral SA32.
(d) The integral SB31 is smaller than the integral SB32.
(e) The integral SC31 is larger than the integral SC32.
(f) The integral SA31 is larger than the integral SB31.
(g) The integral SA31 is smaller than the integral SB32.
(h) The integral SA31 is smaller than the integral SC31.
(i) The integral SA31 is larger than the integral SC32.
(j) The integral SA32 is larger than the integral SB31.
(k) The integral SA32 is smaller than the integral SB32.
(l) The integral SA32 is smaller than the integral SC31.
(m) The integral SA32 is larger than the integral SC32.
(n) The integral SB31 is smaller than the integral SC31.
(o) The integral SB31 is equal to the integral SC32.
(p) The integral SB32 is larger than the integral SC31.
(q) The integral SB32 is larger than the integral SC32.

The optical cosmetic device 10 for body hair in the third embodiment has advantages similar to advantages (1) to (22) of the optical cosmetic device 10 for body hair in the first embodiment. More specifically, the optical cosmetic device 10 in the third embodiment is less likely to cause unwanted side effects on the skin and can inhibit the growth of body hair and has other various advantages. The optical cosmetic device 10 for body hair in the third embodiment further has the advantages described below.

(24) The integral SB31 of the cosmetic light for body hair is smaller than the integral SB11. The inventors of the present application have determined through experiments that the characteristic cosmetic light for body hair has the following advantage. The cosmetic light for body hair is more likely to reduce the unwanted side effects on the skin than when the integral SB31 is larger than the integral SB11.

The present invention is not limited to the first to third embodiments and may be modified in the following forms.

The cosmetic light for body hair according to the first embodiment has the first peak P11 and the second peak P12 in the first wavelength range WL1. However, the number of peaks formed in the first wavelength range WL1 is not limited to the number specified in the first embodiment. Cosmetic light for body hair in a modification does not include at least one of the first peak P11 and the second peak P12. Cosmetic light for body hair in another modification has at least one additional peak other than the first peak P11 and the second peak P12 in the first wavelength range WL1. With the number of peaks in the first wavelength range WL1 differing from the first embodiment, the optical cosmetic device at least has advantages similar to advantages (1) to (3) of the first embodiment when the integral SL11 is smaller than the integral SL12.

The cosmetic light for body hair according to the first embodiment has the third peak P13 in the second wavelength range WL2. However, the number of peaks formed in the second wavelength range WL2 is not limited to the number specified in the first embodiment. Cosmetic light for body hair in a modification may eliminate the third peak P13. Cosmetic light for body hair in another embodiment has at least one peak other than the third peak P13 in the second wavelength range WL2. With the number of peaks in the second wavelength range WL2 differing from the first embodiment, the optical cosmetic device has at least advantages (1) to (3) of the first embodiment.

The cosmetic light for body hair in the first embodiment has no peaks in the third wavelength range WL3. However, the number of peaks in the third wavelength range WL3 is not limited to the number specified in the first embodiment. Cosmetic light for body hair in a modification may include at least one peak in the third wavelength range WL3. The peak in the third wavelength range WL3 is preferably smaller than the peak in the first wavelength range WL1. The peak in the third wavelength range WL3 is preferably smaller than the peak in the second wavelength range WL2. Even if the number of peaks in the third wavelength range WL3 differs from the first embodiment, the optical cosmetic device has at least advantages (1) to (3) of the first embodiment when the integral SL11 is smaller than the integral SL12.

The cosmetic light for body hair in the first embodiment has the third peak P13 that is larger than the second peak P12. The relationship between the peaks is not limited to the relationship described in the first embodiment. Cosmetic light for body hair in a modification may have the third peak P13 that is smaller than or equal to the second peak P12.

Cosmetic light for body hair in the second embodiment has the first peak P21 and the second peak P22 in the first wavelength range WL1. However, the number of peaks formed in the first wavelength range WL1 is not limited to the number specified in the second embodiment. Cosmetic light for body hair in a modification may eliminate at least one of the first peak P21 and the second peak P22. Cosmetic light for body hair in another modification has at least one peak other than the first peak P21 and the second peak P22 in the first wavelength range WL1. Even if the number of peaks in the first wavelength range WL1 differs from the second embodiment, the optical cosmetic device has at least advantages similar to advantages (1) to (3) of the second embodiment when the integral SL21 is smaller than the integral SL22.

The cosmetic light for body hair in the second embodiment has the third peak P23 in the second wavelength range WL2. However, the number of peaks formed in the second wavelength range WL2 is not limited to the number specified in the second embodiment. Cosmetic light for body hair in a modification may eliminate the third peak P22. Cosmetic light for body hair in another modification has at least one peak other than the third peak P23 in the second wavelength range WL2. Even if the number of peaks in the second wavelength range WL2 differs from the second embodiment, the optical cosmetic device has at least advantages similar to advantages (1) to (3) of the second embodiment when the integral SL21 is smaller than the integral SL22.

The cosmetic light for body hair in the second embodiment has no peaks in the third wavelength range WL3. However, the number of peaks formed in the third wavelength range WL3 is not limited to the number specified in the second embodiment. Cosmetic light for body hair in a modification may include at least one peak in the third wavelength range WL3. The peak in the third wavelength range WL3 is preferably smaller than the peak in the first wavelength range WL1. The peak in the third wavelength range WL3 is preferably smaller than the peak in the second wavelength range WL2. With the number of peaks in the third wavelength range WL3 differing from the second embodiment, the optical cosmetic device has at least advantages similar to advantages (1) to (3) of the second embodiment when the integral SL21 is smaller than the integral SL22.

The cosmetic light for body hair in the second embodiment has the third peak P23 that is larger than the second peak P22. The relationship between the peaks is not limited to the relationship described in the second embodiment. Cosmetic light for body hair in a modification may have the third peak P23 that is smaller than or equal to the second peak P22.

The cosmetic light for body hair in the third embodiment has the first peak P31 and the second peak P32 in the first wavelength range WL1. However, the number of peaks formed in the first wavelength range WL1 is not limited to the number specified in the third embodiment. Cosmetic light for body hair in a modification may eliminate at least one of the first peak P31 and the second peak P32. Cosmetic light for body hair in to another modification has at least one peak other than the first peak P31 and the second peak P32 in the first wavelength range WL1. Even if the number of peaks in the first wavelength range WL1 differs from the third embodiment, the optical cosmetic device has at least advantages similar to advantages (1) to (3) of the third embodiment when the integral SL31 is smaller than the integral SL32.

The cosmetic light for body hair in the third embodiment has the third peak P33 and the fourth peak P34 in the second wavelength range WL2. However, the number of peaks formed in the second wavelength range WL2 is not limited to the number specified in the third embodiment. Cosmetic light for body hair in a modification may eliminate at least one of the third peak P33 and the fourth peak P34. Cosmetic light for body hair in another modification has at least one peak other than the third peak P33 and the fourth peak P34 in the second wavelength range WL2. Even if the number of peaks in the second wavelength range WL2 differs from the third embodiment, the optical cosmetic device has at least advantages similar to advantages (1) to (3) of the third embodiment when the integral SL31 is smaller than the integral SL32.

The cosmetic light for body hair in the third embodiment has no peaks in the third wavelength range WL3. However, the number of peaks formed in the third wavelength range WL3 is not limited to the number specified in the third embodiment. Cosmetic light for body hair in a modification may include at least one peak in the third wavelength range WL3. The peak in the third wavelength range WL3 is preferably smaller than the peak in the first wavelength range WL1. The peak in the third wavelength range WL3 is preferably smaller than the peak in the second wavelength range WL2. Even if the number of peaks in the third wavelength range WL3 differs from the third embodiment, the optical cosmetic device has at least advantages similar to advantages (1) to (3) of the third embodiment when the integral SL31 is smaller than the integral SL32.

The cosmetic light for body hair in the third embodiment has the third peak P33 that is larger than the second peak P32. The relationship between the peaks is not limited to the relationship described in the third embodiment. Cosmetic light for body hair in a modification has the third peak P33 that is smaller than or equal to the second peak P32.

The cosmetic light for body hair in the third embodiment has the fourth peak P34 that is smaller than the second peak P32. The relationship between the peaks is not limited to the relationship described in the third embodiment. Cosmetic light for body hair in a modification may have the fourth peak P34 that is larger than or equal to the second peak P32.

The cosmetic light for body hair in the third embodiment has the fourth peak P34 that is smaller than the third peak P33. The relationship between the peaks is not limited to the relationship described in the third embodiment. Cosmetic light for body hair in a modification has the fourth peak P34 that is larger than or equal to the third peak P33.

The cosmetic light for body hair in each of the first to third embodiments contains components having wavelengths longer than 700 nm. However, the spectrum of light having a wavelength longer than 700 nm is not limited to the spectrum described in each of the embodiments. Cosmetic light for body hair in a modification may completely contain no components having a wavelength longer than, for example, 700 nm.

The optical cosmetic device 10 for body hair in each of the first to third embodiments defines the wavelength range of 400 to 500 nm as the first wavelength range WL1. However, the first wavelength range WL1 is not limited to the range specified in each of the above embodiments. The first wavelength range WL1 in a modification may be a wavelength range not shorter than 400 nm and shorter than 500 nm, a wavelength range longer than 400 nm and shorter than 500 nm, or a wavelength range longer than 400 nm and not longer than 500 nm.

The optical cosmetic device 10 for body hair in each of the first to third embodiments defines the wavelength range of 500 to 600 nm as the second wavelength range WL2. However, the second wavelength range WL2 is not limited to the range specified in each of the above embodiments. The second wavelength range WL2 in a modification may be a wavelength range not shorter than 500 nm and shorter than 600 nm, a wavelength range longer than 500 nm and shorter than 600 nm, or a wavelength range longer than 500 nm and not longer than 600 nm.

The optical cosmetic device 10 for body hair in each of the first to third embodiments defines the wavelength range of 600 to 700 nm as the third wavelength range WL3. However, the third wavelength range WL3 is not limited to the range specified in each of the above embodiments. The third wavelength range WL3 in a modification is, for example, a wavelength range not shorter than 600 nm and shorter than 700 nm, a wavelength range longer than 600 nm and shorter than 700 nm, or a wavelength range longer than 600 nm and not longer than 700 nm.

The optical cosmetic device 10 for body hair in each of the first to third embodiments includes the lens 36 formed from acrylic, polycarbonate, or glass. However, the composition of the lens 36 is not limited to the composition specified in each of the above embodiments. The lens according to a modification includes a base containing a light absorbing material.

In the optical cosmetic device 10 for body hair in each of the first to third embodiments, the structures of the lens 36 and the optical filter 37 are not limited to the structures specified in each embodiment. The optical cosmetic device for body hair in a modification may include a lens integrated with an optical filter.

The optical cosmetic device 10 for body hair includes the optical system including the light source 34, the wavelength selector such as the optical filter 37, and the lens 36. The optical cosmetic device 10 may eliminate one or both of the optical filter 37 and the lens 36 as long as the optical system can emit cosmetic light for body hair.

The optical cosmetic device 10 for body hair in each of the first to third embodiments defines the intensity of the cosmetic light for body hair by using the spectral radiant energy density. However, the intensity of the cosmetic light for body hair should not be limited to the intensity specified in each of the above embodiments. In one example, the intensity of the cosmetic light for body hair may be defined by using a relative intensity.

Some of the above embodiments and modifications may be combined freely as long as there are technical contradictions.

EXAMPLES

Through experiments, the inventors of the present application have studied the influence of cosmetic light for body hair in each of the first to third embodiments and a comparative example on body hair.

Figure 8:
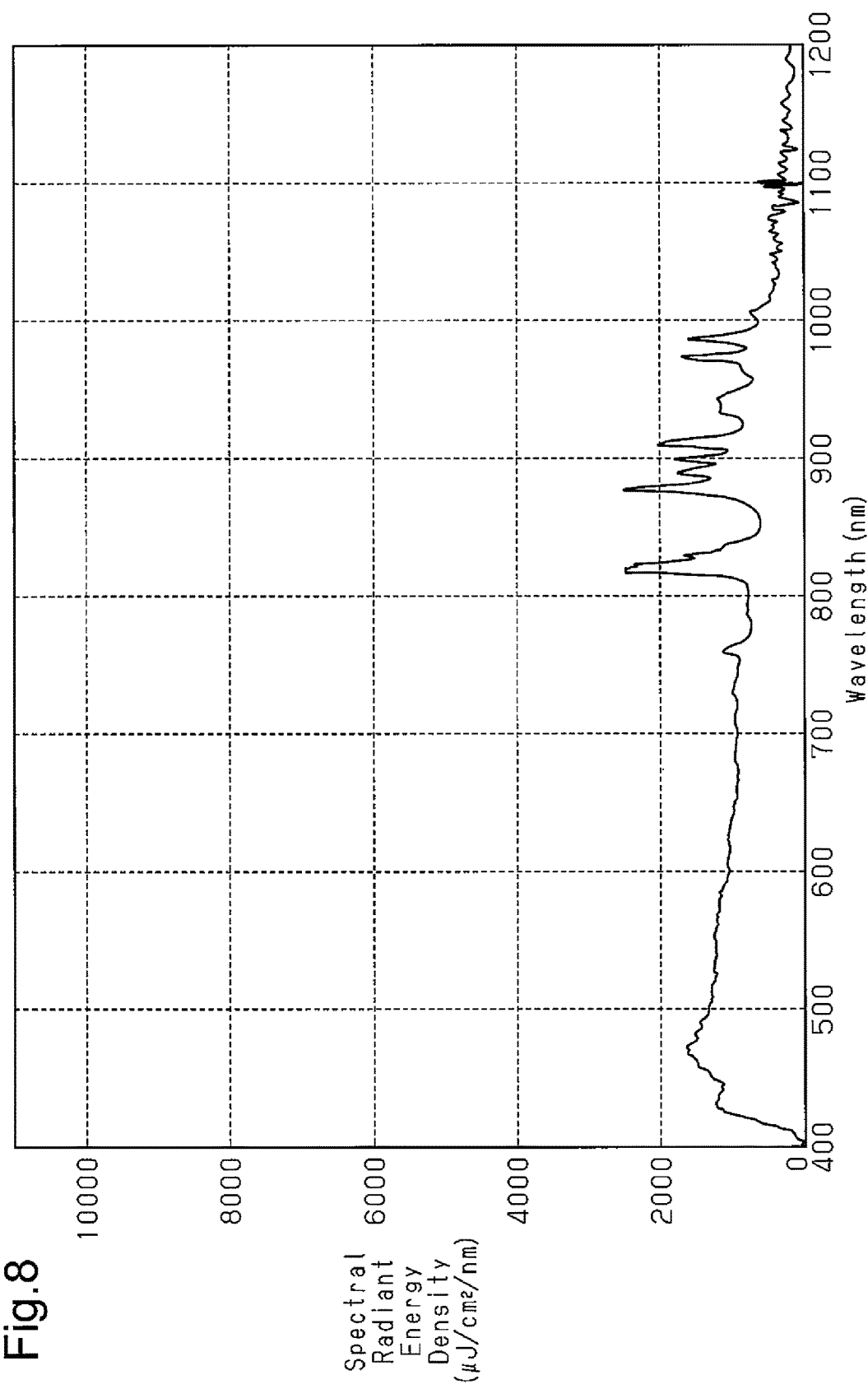
FIG. 8 is a graph showing the spectrum of light emitted from a device of a comparative example.

The comparative example uses a device that differs from the optical cosmetic device 10 of each of the embodiments only in the type of the lens 36 and the optical filter 3. FIG. 8 shows the spectrum of light emitted from the device of the comparative example.

Body hair was shaved from a predetermined portion in each back of five experimental mice, which were irradiated with light, to form a square observation area. Each side of the square observation area was 2 cm. In the same manner as the mice irradiated with light, observation areas were formed in five control mice, which were not irradiated with light.

In each of the experiments conducted under different conditions, the experimental mice, or light irradiated mice, were irradiated with light, whereas the control mice, or non-light irradiated mice, were not irradiated with light. For each experimental mouse, the growth of body hair and changes in the skin in the observation area were observed after the light irradiation. For each control mouse, the growth of body hair and changes in the skin in the observation area were also observed as the same timing.

The number of body hairs and the length of the hairs in the observation area were measured through an image analysis of the observation area. The measured number of body hairs was multiplied by the total length of the hairs to obtain the body hair amount.

The average body hair amount for the light irradiated mice was divided by the average body hair amount for the non-light irradiated mice to yield the ratio of hair growth inhibition.

The hair growth inhibition ratio of 1 indicates that the growth of body hair of the light irradiated mice is the same as the growth of body hair of the non-light irradiated mice. The hair growth inhibition ratio closer to 0 indicates that the growth of body hair of the light irradiated mice is slower than the growth of body hair of the non-light irradiated mice, thus indicating that the light has a higher effect of inhibiting the growth of hair.

The experimental conditions were set in the manner described below. The conditions include the light energy density, the irradiation time, the irradiation cycle, the unit number of times of irradiation, the total number of times of irradiation, the observation start period, and the progress observation period.

The light energy density was set to three values, namely, 0.2 (J/cm$^2$), 1.0 (J/cm$^2$), and 1.5 (J/cm$^2$). The light energy density can be changed by supplying a different amount of power to the light source 34.

The irradiation time was set to three values, namely, 0.6 ms, 1.0 ms, and 2.0 ms. The irradiation time can be changed by providing a different signal from the control unit 50 to the light source 34.

The irradiation cycle was set to two values, namely, 30 seconds and 60 seconds. The irradiation cycle can be changed by providing a different signal from the control unit 50 to the light source 34.

The unit number of times of irradiation was set to two values, namely, 4 times/day and 8 times/day. The experiments were conducted for four days. The total number of times of irradiation was thus 16 times and 32 times.

In the observation start period immediately after the formation of the observation areas in the light irradiated mice and the non-light irradiated mice, these mice underwent the first irradiation in their observation areas. The images of the observation areas were captured at the end of the final irradiation (referred to as immediately after the irradiation), one week after the irradiation, and two weeks after the irradiation. The period during which the images were captured may be referred to as the observation period.

Table 1 shows the results under the irradiation cycle of 30 s, the number of irradiation times of 4 times/day, and the total number of irradiation times of 16 times.

Table 2 shows the results under the irradiation cycle of 30 s, the number of irradiation times of 8 times/day, and the total number of irradiation times of 32 times.

Table 3 shows the results under the irradiation cycle of 60 s, the number of irradiation times of 4 times/day, and the total number of irradiation times of 16 times.

Table 4 shows the results under the irradiation cycle of 60 s, the number of irradiation times of 8 times/day, and the total number of irradiation times of 32 times.

TABLE 1

| Light energy density (J/cm$^2$) | Irradiation time (ms) | Progress observation period | Hair growth inhibition ratio (Light irradiated hair amount/ non-light irradiated hair amount) | | | |
|---|---|---|---|---|---|---|
| | | | 1st embodiment | 2nd embodiment | 3rd embodiment | Comp. ex. |
| 0.2 | 0.6 | Immediately after irradiation | 0.8 | 0.7 | 0.7 | 0.8 |
| | | After one week | 0.7 | 0.6 | 0.5 | 0.7 |
| | | After two weeks | 0.5 | 0.4 | 0.4 | 0.8 |
| | 1 | Immediately after irradiation | 0.8 | 0.7 | 0.7 | 0.8 |
| | | After one week | 0.7 | 0.6 | 0.5 | 0.7 |
| | | After two weeks | 0.5 | 0.4 | 0.4 | 0.7 |
| | 2 | Immediately after irradiation | 0.8 | 0.7 | 0.7 | 0.8 |
| | | After one week | 0.7 | 0.6 | 0.5 | 0.7 |
| | | After two weeks | 0.5 | 0.4 | 0.4 | 0.7 |
| 1 | 0.6 | Immediately after irradiation | 0.7 | 0.7 | 0.7 | 0.8 |
| | | After one week | 0.6 | 0.6 | 0.5 | 0.7 |
| | | After two weeks | 0.5 | 0.4 | 0.4 | 0.8 |
| | 1 | Immediately after irradiation | 0.7 | 0.7 | 0.7 | 0.8 |
| | | After one week | 0.6 | 0.6 | 0.5 | 0.7 |
| | | After two weeks | 0.5 | 0.4 | 0.4 | 0.7 |
| | 2 | Immediately after irradiation | 0.7 | 0.7 | 0.7 | 0.8 |
| | | After one week | 0.7 | 0.6 | 0.5 | 0.7 |
| | | After two weeks | 0.4 | 0.4 | 0.4 | 0.7 |
| 1.5 | 0.6 | Immediately after irradiation | 0.6 | 0.6 | 0.6 | 0.7 |
| | | After one week | 0.5 | 0.6 | 0.5 | 0.6 |
| | | After two weeks | 0.4 | 0.4 | 0.4 | 0.7 |
| | 1 | Immediately after irradiation | 0.6 | 0.7 | 0.6 | 0.7 |
| | | After one week | 0.6 | 0.5 | 0.5 | 0.7 |
| | | After two weeks | 0.4 | 0.4 | 0.4 | 0.7 |
| | 2 | Immediately after irradiation | 0.6 | 0.7 | 0.6 | 0.7 |
| | | After one week | 0.6 | 0.5 | 0.4 | 0.6 |
| | | After two weeks | 0.3 | 0.4 | 0.4 | 0.6 |

*Irradiation cycle = 30 s, Unit irradiation times = 4 times/day, Total irradiation times = 16 times

TABLE 2

| Light energy density (J/cm$^2$) | Irradiation time (ms) | Progress observation period | Hair growth inhibition ratio (Light irradiated hair amount/ non-light irradiated hair amount) | | | |
|---|---|---|---|---|---|---|
| | | | 1st embodiment | 2nd embodiment | 3rd embodiment | Comp. ex. |
| 0.2 | 0.6 | Immediately after irradiation | 0.7 | 0.7 | 0.7 | 0.8 |
| | | After one week | 0.7 | 0.5 | 0.5 | 0.7 |
| | | After two weeks | 0.5 | 0.4 | 0.4 | 0.8 |
| | 1 | Immediately after irradiation | 0.7 | 0.7 | 0.7 | 0.8 |
| | | After one week | 0.7 | 0.5 | 0.5 | 0.7 |
| | | After two weeks | 0.5 | 0.4 | 0.4 | 0.7 |
| | 2 | Immediately after irradiation | 0.7 | 0.7 | 0.7 | 0.8 |
| | | After one week | 0.7 | 0.5 | 0.5 | 0.7 |
| | | After two weeks | 0.5 | 0.4 | 0.4 | 0.7 |
| 1 | 0.6 | Immediately after irradiation | 0.7 | 0.7 | 0.7 | 0.8 |
| | | After one week | 0.7 | 0.6 | 0.5 | 0.7 |
| | | After two weeks | 0.5 | 0.4 | 0.4 | 0.8 |
| | 1 | Immediately after irradiation | 0.7 | 0.7 | 0.7 | 0.8 |
| | | After one week | 0.7 | 0.5 | 0.5 | 0.7 |
| | | After two weeks | 0.5 | 0.4 | 0.4 | 0.7 |
| | 2 | Immediately after irradiation | 0.7 | 0.7 | 0.7 | 0.8 |
| | | After one week | 0.6 | 0.5 | 0.5 | 0.7 |
| | | After two weeks | 0.4 | 0.4 | 0.4 | 0.7 |
| 1.5 | 0.6 | Immediately after irradiation | 0.6 | 0.6 | 0.6 | 0.7 |
| | | After one week | 0.5 | 0.6 | 0.5 | 0.6 |
| | | After two weeks | 0.4 | 0.4 | 0.4 | 0.7 |
| | 1 | Immediately after irradiation | 0.6 | 0.7 | 0.6 | 0.7 |
| | | After one week | 0.6 | 0.5 | 0.5 | 0.7 |
| | | After two weeks | 0.4 | 0.4 | 0.4 | 0.7 |
| | 2 | Immediately after irradiation | 0.6 | 0.7 | 0.6 | 0.7 |
| | | After one week | 0.6 | 0.5 | 0.4 | 0.6 |
| | | After two weeks | 0.5 | 0.4 | 0.4 | 0.6 |

*Irradiation cycle = 30 s, Unit irradiation times = 8 times/day, Total irradiation times = 32 times

TABLE 3

| Light energy density (J/cm$^2$) | Irradiation time (ms) | Progress observation period | Hair growth inhibition ratio (Light irradiated hair amount/ non-light irradiated hair amount) | | | |
|---|---|---|---|---|---|---|
| | | | 1st embodiment | 2nd embodiment | 3rd embodiment | Comp. ex. |
| 0.2 | 0.6 | Immediately after irradiation | 0.8 | 0.7 | 0.7 | 0.8 |
| | | After one week | 0.7 | 0.6 | 0.5 | 0.7 |
| | | After two weeks | 0.5 | 0.4 | 0.4 | 0.8 |
| | 1 | Immediately after irradiation | 0.8 | 0.7 | 0.7 | 0.8 |
| | | After one week | 0.7 | 0.6 | 0.5 | 0.7 |
| | | After two weeks | 0.5 | 0.4 | 0.4 | 0.7 |
| | 2 | Immediately after irradiation | 0.8 | 0.7 | 0.7 | 0.8 |
| | | After one week | 0.7 | 0.6 | 0.5 | 0.7 |
| | | After two weeks | 0.5 | 0.4 | 0.4 | 0.7 |
| 1 | 0.6 | Immediately after irradiation | 0.8 | 0.7 | 0.7 | 0.8 |
| | | After one week | 0.7 | 0.6 | 0.5 | 0.7 |
| | | After two weeks | 0.5 | 0.4 | 0.4 | 0.8 |
| | 1 | Immediately after irradiation | 0.8 | 0.7 | 0.7 | 0.8 |
| | | After one week | 0.7 | 0.6 | 0.5 | 0.7 |
| | | After two weeks | 0.5 | 0.4 | 0.4 | 0.7 |
| | 2 | Immediately after | 0.8 | 0.7 | 0.7 | 0.8 |

TABLE 3-continued

| Light energy density (J/cm 2) | Irradiation time (ms) | Progress observation period | Hair growth inhibition ratio (Light irradiated hair amount/ non-light irradiated hair amount) | | | |
|---|---|---|---|---|---|---|
| | | | 1st embodiment | 2nd embodiment | 3rd embodiment | Comp. ex. |
| | | irradiation | | | | |
| | | After one week | 0.7 | 0.6 | 0.5 | 0.7 |
| | | After two weeks | 0.4 | 0.4 | 0.4 | 0.7 |
| 1.5 | 0.6 | Immediately after irradiation | 0.6 | 0.6 | 0.6 | 0.7 |
| | | After one week | 0.5 | 0.6 | 0.5 | 0.6 |
| | | After two weeks | 0.4 | 0.4 | 0.4 | 0.7 |
| | 1 | Immediately after irradiation | 0.6 | 0.7 | 0.6 | 0.7 |
| | | After one week | 0.6 | 0.5 | 0.5 | 0.7 |
| | | After two weeks | 0.4 | 0.4 | 0.4 | 0.7 |
| | 2 | Immediately after irradiation | 0.6 | 0.7 | 0.6 | 0.7 |
| | | After one week | 0.6 | 0.5 | 0.4 | 0.6 |
| | | After two weeks | 0.5 | 0.4 | 0.4 | 0.6 |

*Irradiation cycle = 60 s, Unit irradiation times = 4 times/day, Total irradiation times = 16 times

TABLE 4

| Light energy density (J/cm 2) | Irradiation time (ms) | Progress observation period | Hair growth inhibition ratio (Light irradiated hair amount/ non-light irradiated hair amount) | | | |
|---|---|---|---|---|---|---|
| | | | 1st embodiment | 2nd embodiment | 3rd embodiment | Comp. ex. |
| 0.2 | 0.6 | Immediately after irradiation | 0.7 | 0.7 | 0.7 | 0.8 |
| | | After one week | 0.7 | 0.5 | 0.5 | 0.7 |
| | | After two weeks | 0.5 | 0.4 | 0.4 | 0.8 |
| | 1 | Immediately after irradiation | 0.7 | 0.7 | 0.7 | 0.8 |
| | | After one week | 0.7 | 0.5 | 0.5 | 0.7 |
| | | After two weeks | 0.5 | 0.4 | 0.4 | 0.7 |
| | 2 | Immediately after irradiation | 0.7 | 0.7 | 0.7 | 0.8 |
| | | After one week | 0.7 | 0.5 | 0.5 | 0.7 |
| | | After two weeks | 0.5 | 0.4 | 0.4 | 0.7 |
| 1 | 0.6 | Immediately after irradiation | 0.7 | 0.7 | 0.7 | 0.8 |
| | | After one week | 0.7 | 0.6 | 0.5 | 0.7 |
| | | After two weeks | 0.5 | 0.4 | 0.4 | 0.8 |
| | 1 | Immediately after irradiation | 0.7 | 0.7 | 0.7 | 0.8 |
| | | After one week | 0.7 | 0.5 | 0.5 | 0.7 |
| | | After two weeks | 0.5 | 0.4 | 0.4 | 0.7 |
| | 2 | Immediately after irradiation | 0.7 | 0.7 | 0.7 | 0.8 |
| | | After one week | 0.6 | 0.5 | 0.5 | 0.7 |
| | | After two weeks | 0.4 | 0.4 | 0.4 | 0.7 |
| 1.5 | 0.6 | Immediately after irradiation | 0.6 | 0.6 | 0.6 | 0.7 |
| | | After one week | 0.5 | 0.6 | 0.5 | 0.6 |
| | | After two weeks | 0.4 | 0.4 | 0.4 | 0.7 |
| | 1 | Immediately after irradiation | 0.6 | 0.7 | 0.6 | 0.7 |
| | | After one week | 0.6 | 0.5 | 0.5 | 0.7 |
| | | After two weeks | 0.4 | 0.4 | 0.4 | 0.7 |
| | 2 | Immediately after irradiation | 0.6 | 0.7 | 0.6 | 0.7 |
| | | After one week | 0.6 | 0.5 | 0.4 | 0.6 |
| | | After two weeks | 0.5 | 0.4 | 0.4 | 0.6 |

*Irradiation cycle = 60 s, Unit irradiation times = 8 times/day, Total irradiation times = 32 times The tables show that the hair growth inhibition ratio of each of the first to third embodiments and the comparative example is smaller as the light energy density increases. The hair growth inhibition ratio of each of the first to third embodiments is substantially smaller than the ratio of the comparative example immediately after the irradiation and thereafter. The hair growth inhibition ratio of each of the first to third embodiments approaches 0 as the time elapses immediately after the irradiation. This increases the gap between the hair growth inhibition ratio of the embodiments and the hair growth inhibition ratio of the comparative example. More specifically, the cosmetic light for body hair in each of the first to third embodiments maintains the cosmetic treatment effect of body hair over a longer period of time than the light of the comparative example.

The skin in the observation areas of the light irradiated mice and the non-light irradiated mice was observed to quantitatively evaluate the influence of the cosmetic light for body hair of the first to third embodiments and the comparative example on the skin.

For the evaluation, a granular layer was collected from the skin of the observation area of each mouse immediately after the irradiation. The granular layers from the light irradiated mice were compared with the granular layers from the non-light irradiated mice. The granular layers from the light irradiated mice irradiated with the cosmetic light for body hair of the embodiments differ insignificantly from the granular layers from the non-light irradiated mice. The granular layers from the light irradiated mice irradiated with the light of the comparative example differ significantly from the granular layers from the non-light irradiated mice. This finding indicates that the influence of the light of the comparative example is greater than the influence of the cosmetic light for body hair of the embodiments.

Supplemental Claim 1

The optical cosmetic device for body hair according to any one of claims 1 to 6, wherein the intensity integral of cosmetic light for body hair is larger in a wavelength range of 500 to 600 nm than in a wavelength range of 600 to 700 nm. The optical cosmetic device for body hair with this structure achieves a higher body hair cosmetic treatment effect than a referential example in which the intensity integral is smaller in the wavelength range of 500 to 600 nm than in the wavelength range of 600 to 700 nm.

Supplemental Claim 2

The optical cosmetic device for body hair according to any one of claims 1 to 6 and supplemental claim 1, wherein the intensity integral of cosmetic light for body hair is larger in a wavelength range of 400 to 500 nm than in a wavelength range of 600 to 700 nm. The optical cosmetic device for body hair with this structure achieves a higher body hair cosmetic treatment effect than when the intensity integral is smaller in the wavelength range of 400 to 500 nm than in the wavelength range of 600 to 700 nm.

Supplemental Claim 3

The optical cosmetic device for body hair according to any one of claims 1 to 6 and supplemental claims 1 and 2, wherein the intensity integral of cosmetic light for body hair is larger in a wavelength range of 500 to 530 nm than in a wavelength range of 570 to 600 nm. The optical cosmetic device for body hair with this structure achieves a higher body hair cosmetic treatment effect than when the intensity integral is smaller in the wavelength range of 500 to 530 nm than in the wavelength range of 570 to 600 nm.

Supplemental Claim 4

In the optical cosmetic device for body hair according to any one of claims 1 to 6 and supplemental claims 1 to 3, wherein the cosmetic light for body hair has a first peak in a wavelength range of 440 to 460 nm. The first peak has the smallest value of a plurality of peaks included in a wavelength range of 400 to 700 nm. The optical cosmetic device for body hair with this structure is less likely to cause unwanted side effects on the skin than when the first peak is larger than other peaks included in the wavelength range of 400 to 700 nm.

Supplemental Claim 5

The optical cosmetic device for body hair according to supplemental claim 4, wherein the first peak has the smallest value of a plurality of peaks included in a wavelength range of 400 to 600 nm. The optical cosmetic device for body hair with this structure is less likely to cause unwanted side effects on the skin than when the first peak is larger than other peaks included in the wavelength range of 400 to 600 nm.

Supplemental Claim 6

The optical cosmetic device for body hair according to any one of claims 1 to 6 or according to one of supplemental claims 1 to 5, wherein the cosmetic light for body hair has a second peak in a wavelength range of 480 to 500 nm. The second peak has the second largest value of a plurality of peaks included in a wavelength range of 400 to 700 nm. The optical cosmetic device for body hair with this structure achieves a higher body hair cosmetic treatment effect than when the second peak is a value smaller than or equal to the third largest value of the peaks included in the wavelength range of 400 to 700 nm.

Supplemental Claim 7

The optical cosmetic device for body hair according to supplemental claim 6, wherein the second peak has the second largest value of a plurality of peaks included in the wavelength range of 400 to 600 nm. The optical cosmetic device for body hair with this structure achieves a higher body hair cosmetic treatment effect than when the second peak is a value that is smaller than or equal to the third largest value of the peaks included in the wavelength range of 400 to 600 nm.

Supplemental Claim 8

The optical cosmetic device for body hair according to any one of claims 1 to 6 and supplemental claims 1 to 7, wherein the cosmetic light for body hair has a first peak in a wavelength range of 440 to 460 nm. The cosmetic light for body hair has a second peak in a wavelength range of 480 to 500 nm. The second peak has an intensity of at least twice an intensity of the first peak. The optical cosmetic device for body hair with this structure achieves a higher body hair cosmetic treatment effect than when the second peak has a smaller intensity than twice the intensity of the first peak.

Supplemental Claim 9

The optical cosmetic device for body hair according to any one of claims 1 to 6 and supplemental claims 1 to 8, wherein the cosmetic light for body hair has a third peak in a wavelength range of 520 to 540 nm. The third peak has the largest value of a plurality of peaks included in a wavelength range of 400 to 700 nm. The optical cosmetic device for body hair with this structure achieves a higher body hair cosmetic treatment effect than when the third peak is a value that is smaller than or equal to the second largest value of the peaks included in the wavelength range of 400 to 700 nm.

Supplemental Claim 10

The optical cosmetic device for body hair according to supplemental claim 9, wherein the third peak has the largest value of a plurality of peaks included in a wavelength range of 400 to 600 nm. The optical cosmetic device for body hair with this structure achieves a higher body hair cosmetic treatment effect than when the third peak is a value that is smaller than or equal to the second largest value of the peaks included in the wavelength range of 400 to 600 nm.

Supplemental Claim 11

The optical cosmetic device for body hair according to any one of claims 1 to 6 and supplemental claims 1 to 10, wherein the cosmetic light for body hair has a first peak in a wavelength range of 440 to 460 nm. The cosmetic light for body hair has a third peak in a wavelength range of 520 to 540 nm. The third peak has an intensity that is greater than or equal to an intensity of twice an intensity of the first peak. The optical cosmetic device for body hair with this structure achieves a higher body hair cosmetic treatment effect than a referential example in which the third peak has a smaller intensity than twice the intensity of the first peak.

Supplemental Claim 12

The optical cosmetic device for body hair according to any one of claims 1 to 6 and supplemental claims 1 to 11, wherein the cosmetic light for body hair has the largest increasing rate for a wavelength range of 400 to 700 nm that falls within a wavelength range of 480 to 500 nm. The optical cosmetic device for body hair with this structure achieves a higher body hair cosmetic treatment effect than a referential example in which the largest increasing rate falls within a wavelength range shorter than in the wavelength range of 480 to 500 nm.

The invention claimed is:

1. An optical cosmetic device for body hair, comprising:
   an optical system configured to emit cosmetic light for body hair, wherein:
   the optical system includes a light source configured to emit light comprising a spectrum, a control unit configured to control at least one of a voltage and a current supplied to the light source, and an optical filter configured to change the spectrum of the light emitted from the light source and to generate the cosmetic light for body hair, which comprises:
   an intensity integral of the cosmetic light for body hair in a wavelength range of 400 to 700 nm is larger than an intensity integral of the cosmetic light for body hair in a wavelength range of 700 to 1200 nm,
   an intensity integral of the cosmetic light for body hair in a wavelength range of 400 to 500 nm is smaller than an intensity integral of the cosmetic light for body in a wavelength range of 500 to 600 nm,
   an intensity integral of the cosmetic light for body hair in a wavelength range of 500 to 530 nm is larger than an intensity integral of the cosmetic light for body hair in a wavelength range of 570 to 600 nm,
   an intensity integral of the cosmetic light for body hair in a wavelength range of 400 to 500 nm is larger than an intensity integral of the cosmetic light for body hair in a wavelength range of 600 to 700 nm, and
   the cosmetic light for body hair is configured to inhibit hair growth in a living body or remove hair from a living body, and is further configured to inhibit unwanted side effects including skin inflammation.

2. The optical cosmetic device for body hair according to claim 1, wherein the cosmetic light for body hair includes a plurality of intensity peaks in the wavelength range of 400 to 700 nm, and the largest one of the plurality of intensity peaks is included in the wavelength range of 500 to 570 nm.

3. The optical cosmetic device for body hair according to claim 1, wherein the cosmetic light for body hair comprises a plurality of intensity peaks in the wavelength range of 400 to 700 nm, and the smallest one of the plurality of intensity peaks is included in the wavelength range of 400 to 500 nm.

4. The optical cosmetic device for body hair according to claim 1, wherein the cosmetic light for body hair comprises no intensity peaks in a wavelength range of 400 to 440 nm that includes a first absorbance peak of oxyhemoglobin.

5. The optical cosmetic device for body hair according to claim 1, wherein the cosmetic light for body hair comprises no intensity peaks in a wavelength range of 530 to 570 nm that includes a second absorbance peak of oxyhemoglobin.

6. The optical cosmetic device for body hair according to claim 1, wherein the cosmetic light for body hair comprises an energy density of 0.2 to 1.5 J/cm$^2$.

7. The optical cosmetic device for body hair according to claim 1, wherein an intensity integral of the cosmetic light for body hair in a wavelength range of 500 to 600 nm is larger than an intensity integral of the cosmetic light for body hair in a wavelength range of 600 to 700 nm.

8. The optical cosmetic device for body hair according to claim 1, wherein an intensity integral of the cosmetic light for body hair comprises a first intensity peak in a wavelength range of 440 to 460 nm, and the first intensity peak comprises the smallest value of a plurality of peaks included in a wavelength range of 400 to 700 nm.

9. The optical cosmetic device for body hair according to claim 8, wherein the first intensity peak comprises the smallest value of a plurality of intensity peaks included in a wavelength range of 400 to 600 nm.

10. The optical cosmetic device for body hair according to claim 1, wherein an intensity integral of the cosmetic light for body hair comprises a second intensity peak in a wavelength range of 480 to 500 nm, and the second intensity peak comprises the second largest value of a plurality of intensity peaks included in a wavelength range of 400 to 700 nm.

11. The optical cosmetic device for body hair according to claim 10, wherein the second intensity peak comprises the second largest value of a plurality of intensity peaks included in a wavelength range of 400 to 600 nm.

12. The optical cosmetic device for body hair according to claim 1, wherein an intensity integral of the cosmetic light for body hair comprises a first intensity peak in a wavelength range of 440 to 460 nm and a second intensity peak in a wavelength range of 480 to 500 nm, and the second intensity peak comprises an intensity of at least twice as intensity of the first intensity peak.

13. The optical cosmetic device for body hair according to claim 12, wherein an intensity integral of the cosmetic light for body hair comprises a third intensity peak in a wavelength range of 520 to 540 nm, and the third intensity peak comprises the largest value of a plurality of intensity peaks included in a wavelength range of 400 to 700 nm.

14. The optical cosmetic device for body hair according to claim 13, wherein the third intensity peak comprises the largest value of a plurality of intensity peaks included in a wavelength range of 400 to 600 nm.

15. The optical cosmetic device for body hair according to claim 1, wherein an intensity integral of the cosmetic light for body hair comprises a first intensity peak in a wavelength range of 440 to 460 nm and a third intensity peak in a wavelength range of 520 to 540 nm, and the third intensity peak comprises an intensity that is greater than or equal to an intensity of twice an intensity of the first intensity peak.

16. The optical cosmetic device for body hair according to claim 1, wherein an intensity integral of the cosmetic light for body hair comprises the largest increasing rate for a wavelength range of 400 to 700 nm that falls within a wavelength range of 480 to 500 nm.

* * * * *